US011382658B2

(12) United States Patent
Patel et al.

(10) Patent No.: US 11,382,658 B2
(45) Date of Patent: *Jul. 12, 2022

(54) SURGICAL ROBOTIC ACCESS SYSTEM

(71) Applicant: Applied Medical Resources Corporation, Rancho Santa Margarita, CA (US)

(72) Inventors: Atal C. Patel, Mission Viejo, CA (US); Jeremy J. Albrecht, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 528 days.

This patent is subject to a terminal disclaimer.

(21) Appl. No.: 16/530,745

(22) Filed: Aug. 2, 2019

(65) Prior Publication Data

US 2019/0350620 A1 Nov. 21, 2019

Related U.S. Application Data

(63) Continuation of application No. 15/253,455, filed on Aug. 31, 2016, now Pat. No. 10,368,908.

(Continued)

(51) Int. Cl.
*A61B 17/02* (2006.01)
*A61B 17/34* (2006.01)
(Continued)

(52) U.S. Cl.
CPC ...... *A61B 17/3423* (2013.01); *A61B 17/0218* (2013.01); *A61B 17/3439* (2013.01);
(Continued)

(58) Field of Classification Search
CPC ............ A61B 17/3423; A61B 17/3429; A61B 2034/301; A61B 2034/302; A61B 2034/303; A61B 2034/304
See application file for complete search history.

(56) References Cited

U.S. PATENT DOCUMENTS

| 558,364 A | 4/1896 | Doolittle |
| 958,854 A | 5/1910 | Bunn |

(Continued)

FOREIGN PATENT DOCUMENTS

| DE | 26 05 148 A1 | 8/1977 |
| DE | 33 36 279 C2 | 1/1986 |

(Continued)

OTHER PUBLICATIONS

European Patent Office, The International Search Report and Written Opinion of the International Searching Authority for International Application No. PCT/US2016/049740 titled "Surgical Robotic Access System", dated Nov. 21, 2016, 11 pgs.

(Continued)

*Primary Examiner* — Jan Christopher L Merene
(74) *Attorney, Agent, or Firm* — Thomas Nguyen; Patrick Ikehara

(57) ABSTRACT

The surgical robotic access system provides access for robotic instruments and/or actuators including the introduction, operation and withdrawal of such robotic manipulators into a body cavity without permitting the escape of pressurized fluid or gas. The surgical robotic access system also provides a multi-faceted range of movement without touching or effecting pressure on the opening in the patient's body cavity.

20 Claims, 29 Drawing Sheets

Related U.S. Application Data

(60) Provisional application No. 62/219,042, filed on Sep. 15, 2015.

(51) Int. Cl.

| | | |
|---|---|---|
| *A61B 34/30* | (2016.01) | |
| *A61B 17/00* | (2006.01) | |
| *A61B 34/00* | (2016.01) | |
| *A61B 46/10* | (2016.01) | |
| *A61B 90/40* | (2016.01) | |

(52) U.S. Cl.
CPC .......... *A61B 34/30* (2016.02); *A61B 17/3462* (2013.01); *A61B 17/3474* (2013.01); *A61B 34/70* (2016.02); *A61B 46/10* (2016.02); *A61B 90/40* (2016.02); *A61B 2017/00477* (2013.01); *A61B 2017/3441* (2013.01); *A61B 2017/3466* (2013.01)

(56) References Cited

U.S. PATENT DOCUMENTS

| | | |
|---|---|---|
| 1,157,202 A | 10/1915 | Bates et al. |
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 2,907,321 A | 10/1959 | Rubens |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Banjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |

(56) References Cited

U.S. PATENT DOCUMENTS

| | | |
|---|---|---|
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,144,942 A | 9/1992 | Decarie et al. |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III et al. |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A * | 1/1995 | Hart ............... A61B 17/3462 604/167.03 |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |

(56) References Cited

U.S. PATENT DOCUMENTS

| | | | |
|---|---|---|---|
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A * | 5/1997 | Antoon, Jr. ........ A61B 17/3462 604/256 |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Strouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchiffe et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,007,544 A | 12/1999 | Kim |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A * | 5/2000 | Fox ................ A61B 17/3462 604/167.03 |

(56) References Cited

U.S. PATENT DOCUMENTS

| | | | |
|---|---|---|---|
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 * | 7/2001 | Dennis ............... A61B 17/3462 |
| | | 604/167.03 |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B2 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,041,056 B2 | 5/2006 | Deslauriers et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |

(56) References Cited

U.S. PATENT DOCUMENTS

| | | | |
|---|---|---|---|
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,678,046 B2 | 3/2010 | White et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,822 B2 | 8/2010 | White et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| RE42,379 E | 5/2011 | Loomas |
| 7,951,076 B2 | 5/2011 | Hart et al. |
| 7,998,068 B2 | 8/2011 | Bonadio et al. |
| 8,016,755 B2 | 9/2011 | Ewers et al. |
| 8,021,296 B2 | 9/2011 | Bonadio et al. |
| 8,070,676 B2 | 12/2011 | Ewers et al. |
| 8,105,234 B2 | 1/2012 | Ewers et al. |
| 8,109,873 B2 | 2/2012 | Albrecht et al. |
| 8,142,354 B1 | 3/2012 | Larson et al. |
| 8,187,177 B2 | 5/2012 | Kahle et al. |
| 8,226,552 B2 | 7/2012 | Albrecht et al. |
| 8,235,054 B2 | 8/2012 | Nguyen et al. |
| 8,262,568 B2 | 9/2012 | Albrecht et al. |
| 8,262,622 B2 | 9/2012 | Gonzales et al. |
| 8,267,858 B2 | 9/2012 | Albrecht et al. |
| 8,308,639 B2 | 11/2012 | Albrecht et al. |
| 8,313,431 B2 | 11/2012 | Albrecht et al. |
| 8,317,690 B2 | 11/2012 | Ransden et al. |
| 8,343,047 B2 | 1/2013 | Albrecht et al. |
| 8,388,526 B2 | 3/2013 | Ewers et al. |
| 8,414,487 B2 | 4/2013 | Albrecht et al. |
| RE44,380 E | 7/2013 | de la Torre et al. |
| 8,574,153 B2 | 11/2013 | Shelton |
| 8,647,265 B2 | 2/2014 | Brustad et al. |
| RE44,790 E | 3/2014 | de la Torre et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0049276 A1 | 4/2002 | Zwick |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0082969 A1 | 4/2004 | Kerr |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0230218 A1 | 11/2004 | Criscuolo et al. |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0260246 A1 | 12/2004 | Desmond |
| 2004/0267096 A1 | 12/2004 | Caldwell et al. |
| 2005/0015103 A1 | 1/2005 | Popov |
| 2005/0020884 A1 | 1/2005 | Hart et al. |
| 2005/0033246 A1 | 2/2005 | Ahlbert et al. |
| 2005/0049624 A1 | 3/2005 | Francese et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gozales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |

(56) References Cited

U.S. PATENT DOCUMENTS

| | | |
|---|---|---|
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1* | 10/2005 | Wenchell ............... A61B 1/313 606/108 |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261661 A1* | 11/2005 | McFarlane ......... A61B 17/3462 604/506 |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0200186 A1 | 9/2006 | Marchek et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |
| 2007/0088241 A1 | 4/2007 | Brustad et al. |
| 2007/0088277 A1* | 4/2007 | McGinley .......... A61B 17/0218 604/167.01 |
| 2007/0093695 A1 | 4/2007 | Bonadio et al. |
| 2007/0118175 A1 | 5/2007 | Butler et al. |
| 2007/0135679 A1 | 6/2007 | Hunt et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0005739 A1* | 1/2009 | Hart .................. A61B 17/3462 604/167.06 |
| 2009/0012477 A1 | 1/2009 | Norton et al. |
| 2009/0030375 A1 | 1/2009 | Franer et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0281500 A1 | 11/2009 | Acosta et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1* | 3/2010 | Bonadio ............. A61B 17/3423 600/208 |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0094227 A1 | 4/2010 | Albrecht et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1* | 10/2010 | Widenhouse ...... A61B 17/3462 600/206 |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2011/0071542 A1 | 3/2011 | Prisco et al. |
| 2011/0251466 A1 | 10/2011 | Kleyman et al. |
| 2011/0277775 A1 | 11/2011 | Holop et al. |
| 2012/0095297 A1 | 4/2012 | Dang et al. |
| 2012/0296151 A1 | 11/2012 | Curtis et al. |
| 2012/0310165 A1* | 12/2012 | Hart ................... A61B 17/3462 604/167.03 |
| 2013/0053779 A1 | 2/2013 | Shelton, IV |
| 2014/0039268 A1 | 2/2014 | Richard |
| 2014/0163326 A1 | 6/2014 | Forsell |
| 2014/0276437 A1 | 9/2014 | Hart et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828099 | 12/1999 |
| EP | 0 113 520 | 7/1984 |
| EP | 0 142 262 | 5/1985 |
| EP | 0 487 175 A1 | 5/1992 |
| EP | 0 517 248 | 12/1992 |
| EP | 0 537 768 | 4/1993 |
| EP | 0 542 428 A1 | 5/1993 |
| EP | 0 807 416 | 11/1997 |
| EP | 0 849 517 | 6/1998 |
| EP | 0950376 | 10/1999 |
| EP | 0 980 677 A1 | 2/2000 |
| EP | 1 118 657 | 7/2001 |
| EP | 1 125 552 | 8/2001 |
| EP | 1 312 318 | 5/2003 |
| EP | 1 407 715 | 4/2004 |
| EP | 1 852 053 A1 | 11/2007 |

(56) References Cited

FOREIGN PATENT DOCUMENTS

| | | |
|---|---|---|
| EP | 1 940 282 B1 | 7/2008 |
| EP | 2 044 889 | 4/2009 |
| EP | 1 948 047 | 9/2010 |
| EP | 2 272 449 A2 | 1/2011 |
| EP | 2 272 450 A3 | 1/2011 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S71634 | 2/1997 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 10/1987 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/23536 A1 | 8/1996 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/013803 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2007/109700 A2 | 9/2007 |
| WO | WO 2008/015566 | 2/2008 |
| WO | WO 2008/093313 | 8/2008 |
| WO | WO 2008/121294 | 10/2008 |
| WO | WO 2010/045253 | 4/2010 |
| WO | WO 2010/082722 | 7/2010 |
| WO | WO 2010/104259 | 9/2010 |
| WO | WO 2015/063497 A1 | 5/2015 |

OTHER PUBLICATIONS

U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/927,551, filed Aug. 25, 2004; Title: Surgical Access System, now abandoned.
U.S. Appl. No. 11/330,661, filed Jan. 12, 2006; Title: Sealed Surgical Access Device, now abandoned.
U.S. Appl. No. 12/360,634, filed Jan. 27, 2009; Title: Surgical Access Apparatus and Method, now abandoned.
U.S. Appl. No. 12/004,439, filed Dec. 20, 2007; Title: Skin Seal, now abandoned.
U.S. Appl. No. 12/004,441, filed Dec. 20, 2007; Title: Screw-Type Skin Seal With Inflatable Membrane, now abandoned.
U.S. Appl. No. 10/965,217, filed Oct. 15, 2004; Title: Surgical Sealing Device, now abandoned.
U.S. Appl. No. 10/981,730, filed Nov. 5, 2004; Title: Surgical Sealing Device, now abandoned.
U.S. Appl. No. 11/291,089, filed Dec. 1, 2005; Title: A Surgical Sealing Device, now abandoned.
U.S. Appl. No. 11/785,752, filed Apr. 19, 2007; Title: Instrument Access Device, now abandoned.
U.S. Appl. No. 12/244,024, filed Oct. 2, 2008; Title: Seal Anchor for Use in Surgical Procedures, now abandoned.
U.S. Appl. No. 12/578,832, filed Oct. 14, 2009; Title: Flexible Access Device for Use in Surgical Procedure, now abandoned.
U.S. Appl. No. 10/913,565, filed Aug. 5, 2004; Title: Surgical Device With Tack-Free Gel and Method of Manufacture, now abandoned.

(56) References Cited

OTHER PUBLICATIONS

Dexterity Protractor Instruction Manual by Dexterity Surgical, Inc., dated 1999, 8 pgs.
European Patent Office, European Search Report for European Application No. EP 10 18 4681, entitled "Wound Retraction Apparatus and Method," dated Nov. 22, 2010.
European Patent Office, European Search Report for European Application No. EP 10 18 4608, entitled "Wound Retraction Apparatus and Method," dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method," dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.
European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and the Written Opinion of the International Searching Authority for International Application No. PCT/US2006/040154, entitled, "Method of Making a Hand Access Laparoscopic Device," dated Jan. 30, 2007, 9 pgs.
European Patent Office, International Search Report and the Written Opinion of the International Searching Authority for International Application No. PCT/US2006/040073, entitled, "Split Hoop Wound Retractor," dated Jan. 26, 2007, 8 pgs.
European Patent Office, International Search Report and the Written Opinion of the International Searching Authority for International Application No. PCT/US2006/039905, entitled, "Wound Retractor with Gel Cap," dated Jan. 17, 2007, 8 pgs.
European Patent Office, International Search Report and the Written Opinion of the International Searching Authority for International Application No. PCT/US2006/039883, entitled, "Circular Surgical Retractor," dated Jan. 31, 2007, 8 pgs.
European Patent Office, International Search Report and the Written Opinion of the International Searching Authority for International Application No. PCT/US2006/039800, entitled, "Hand Access Laparoscopic Device," dated Apr. 16, 2007, 14 pgs.
European Patent Office, International Search Report and the Written Opinion of the International Searching Authority for International Application No. PCT/US2006/039799, entitled, "Split Hoop Wound Retractor with Gel Cap," dated Mar. 27, 2007, 11 pgs.
European Patent Office, European Search Report for European Application No. EP 08253236 dated Feb. 10, 2009, 6 pgs.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodenal Cannula for Sheep, Journal of Animal Science, Apr. 1992, vol. 70, Issue 4, pp. 1216-1219.

International Searching Authority/US, International Search Report and the Written Opinion of the International Searching Authority for International Application No. PCT/US04/05484, entitled, "Sealed Surgical Access Device," dated Nov. 12, 2004, 9 pgs.
International Searching Authority/US, International Search Report and the Written Opinion of the International Searching Authority for International Application No. PCT/US01/29682, entitled, "Surgical Access Apparatus and Method," dated Jun. 14, 2002, 8 pgs.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005, 16 pgs.
Office Action in co-pending U.S. Appl. No. 12/360,634, dated Jan. 24, 2011, 12 pages.
Office Action in co-pending U.S. Appl. No. 12/360,710, dated Jan. 24, 2011, 12 pages.
Technical Note: Development of Duodenal Cannula for Sheep, Faculty of Agriculture and School of Medicine Tohokju University, Sendai 981, Japan, dated 1992, 5 pgs.
The International Bureau of WIPO, International Preliminary Report on Patentability for International Application No. PCT/US2004/028250, entitled, "Surgical Instrument Access Device," dated Aug. 29, 2006, 8 pgs.
The International Bureau of WIPO, International Preliminary Report on Patentability for International Application No. PCT/US2006/039799, entitled, "Split Hoop Wound Restractor with Gel Pad," dated Apr. 16, 2008, 7 pgs.
The International Bureau of WIPO, International Preliminary Report on Patentability for International Application No. PCT/US2006/039800, "Hand Access Laparoscopic Device," dated Apr. 16, 2008, 9 pgs.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparoscopic cholecystecomy via two ports, using the "Twin-Port" system, J. Hepatobiliary Pancreat Surg (2001) 8:76-80, dated Feb. 20, 2001.
Declaration of John R. Brustad dated Dec. 10, 2009, submitted in U.S. Appl. No. 11/548,955, including Appendices A-D regarding product sales brochures and production drawings from 2001 and 2005, 7 pgs.
International Search Report and Written Opinion for PCT/IE2005/000113, dated Feb. 22, 2006, 8 pgs.
International Searching Authority—US, International Search Report and Written Opinion of the International Searching Authority for International Application No. PCT/US04/25511, entitled, "Surgical Device with Tack-Free Gel and Method of Manufacture," dated Nov. 7, 2007, 12 pgs.
International Bureau of WIPO, International Report on Patentability for International Application No. PCT/US04/25511, entitled, "Surgical Device with Tack-Free Gel and Method of Manufacture," dated Dec. 6, 2007, 6 pgs.
International Search Report and Written Opinion for PCT/IE2007/000050 dated Aug. 13, 2007, 7 pgs.
The International Searching Authority, The International Search Report and Written Opinion of the International Searching Authority for International Application No. PCT/US08/63445, entitled, "Surgical retractor with Gel Pad," dated Sep. 29, 2008, 11 pgs.
The International Searching Authority, The International Search Report and Written Opinion of the International Searching Authority for International Application No. PCT/US08/063463, entitled, "Surgical Retractor," dated Sep. 10, 2008, 9 pgs.
The International Bureau of WIPO, International Preliminary Report on Patentability for International Application No. PCT/US2008/063463, entitled "Surgical Retractor", dated Nov. 17, 2009, 5 pgs.
The International Bureau of WIPO, International Preliminary Report on Patentability for International Application No. PCT/US08/63445, entitled "Surgical Retractor with Gel Pad", dated Nov. 17, 2009, 5 pgs.

(56) References Cited

OTHER PUBLICATIONS

International Searching Authority—European Patent Office, The International Search Report and Written Opinion for International Application No. PCT/US2009/060540, entitled, "Single Port Access System," dated Feb. 4, 2010, 17 pgs.
The International Bureau of WIPO, International Preliminary Report on Patentability for International Application No. PCT/US2009/060540, entitled, "Single Port Access System," dated Apr. 19, 2011, 8 pgs.
International Searching Authority—European Patent Office, The International Search Report and Written Opinion for International Application No. PCT/US2011/054266, entitled, "Natural Orifice Surgery System," dated Feb. 9, 2012, 13 pgs.
European Patent Office, European Search Report for European Patent No. 11172709.5, entitled, "Sealed Surgical Access Device," dated Aug. 16, 2011, 4 pgs.
European Patent Office, European Search Report for European Patent No. 11172706.1, entitled, "Sealed Surgical Access Device," dated Aug. 16, 2011, 3 pgs.
European Patent Office, European Search Report for European Patent No. 12151288, entitled, "Surgical Instrument Access Device," dated Feb. 10, 2012, 8 pgs.
European Patent Office, Supplementary European Search Report for European Patent Application No. 08755322, entitled, "Surgical Retractor with Gel Pad," dated Apr. 18, 2012, 3 pgs.
European Patent Office, Supplementary European Search Report for European Patent Application No. 08755336, entitled, "Surgical Retractor," dated Jun. 15, 2012, 2 pgs.
Harold W. Harrower, M.D., Isolation of Incisions into Body Cavities, The American Journal of Surgery, vol. 116, pp. 824-826, Dec. 1968.
International Searching Authority—European Patent Office, The International Search Report and Written Opinion for International Application No. PCT/US2013/037213, entitled, "Natural Orifice System," dated Jul. 3, 2013, 9 pgs.
International Searching Authority—European Patent Office, The International Search Report and Written Opinion for International Application No. PCT/US2012/060997, entitled, "Simulated Tissue Structure for Surgical Training," dated Mar. 7, 2013, 8 pgs.
The International Bureau of WIPO, International Preliminary Report on Patentability for International Application No. PCT/US2011/054266, entitled, "Natural Orifice Surgery System" dated Apr. 2, 2013, 8 pgs.
European Patent Office, International Search Report and Written Opinion for International Application No. PCT/US2014/027258, titled Mechanical Gel Surgical Access Device, dated Jun. 3, 2014, 7 pgs.
The International Bureau of WIPO, International Preliminary Report on Patentability for International Application No. PCT/US2013/037213, entitled, "Natural Orifice Surgery System" dated Oct. 21, 2014, 8 pgs.
European Patent Office, The International Search Report and Written Opinion for International Application No. PCT/US2014/056563, entitled "Natural Orifice Access Device," dated Dec. 22, 2014, 13 pgs.
The International Bureau of WIPO, International Preliminary Report on Patentability, for International Application No. PCT/US2014/027258, dated Sep. 24, 2015, 6 pgs.
European Patent Office, European Search Report for European Patent No. 15182203.8, dated Dec. 15, 2015, 4 pgs.
The International Searching Authority, The International Search Report and Written Opinion of the International Searching Authority for International Application No. PCT/US2015/040798 dated Dec. 14, 2015, 21 pgs.
The International Bureau of WIPO, International Preliminary Report on Patentability and Written Opinion for International Application No. PCT/US2014/056563, entitled "Natural Orifice Access Device" dated Mar. 31, 2016, 8 pgs.
The International Bureau of WIPO, International Preliminary Report on Patentability for International Application No. PCT/US2015/040798, entitled, "Gels Having Permanent Tack Free Coatings and Methods of Manufacture" dated Feb. 2, 2017, 14 pgs.
European Patent Office, Extended European Search Report for European Patent No. 17188582.5, entitled, "Single Port Access System," dated Jan. 5, 2018, 8 pgs.
The International Searching Authority, The International Search Report and Written Opinion of the International Searching Authority for International Application No. PCT/US2017/050340, entitled "Surgical Robotic Access System for Irregularly Shaped Robotic Actuators and Associated Robotic Surgical Instruments," dated Feb. 2, 2018, 30 pgs.
European Patent Office, Extended European Search Report for European Application No. EP 19151981.8, entitled "Natural Orifice Surgery System", dated Feb. 27, 2019, 10 pgs.
The International Bureau of WIPO, International Preliminary Report on Patentability for International Application No. PCT/US2017/050340, entitled "Surgical Robotic Access System for Irregularly Shaped Robotic Actuators and Associated Robotic Surgical Instruments," dated Mar. 21, 2019, 20 pgs.
European Patent Office, Extended European Search Report for European Patent No. 19199851.7, entitled, "Mechanical Gel Surgical Access Device," dated Dec. 13, 2019, 9 pgs.

\* cited by examiner

SURGICAL ROBOTIC ACCESS SYSTEM

CROSS-REFERENCE TO RELATED APPLICATIONS

This is a continuation of U.S. patent application Ser. No. 15/253,455, filed Aug. 31, 2016, which claims priority to and benefit of U.S. Provisional Application No. 62/219,042, filed Sep. 15, 2015, the entire disclosures of which are hereby incorporated by reference as if set forth in full herein.

BACKGROUND

This application relates generally to surgical access devices and more particularly to surgical access systems for surgical robotics.

Surgical robotics has been gaining acceptance and seeks to replace or assist in particular surgical procedures. In particular, some assistance provided by surgical robotics seeks to assist in complicated or repetitive tasks. However, surgical robotics provides challenges where procedures performed by a surgeon without robotic assistance would not encounter. One such area is with surgical access devices used in surgery to facilitate the introduction of various surgical instruments into natural biological vessels, conduits, orifices, cavities, and other interior regions of the body. Surgical robotic instruments or actuators impose other restrictions that are not encountered or not a limitation with other surgical instruments or actuators, e.g., a surgeon's hand. Such challenges are further exasperated by the limited or restricted surgical area or environment. For example, the surgical environment may require an introduction of laparoscopic or particular sized instruments or actuators into the abdomen of the body and/or introduced into regions that include fluid or gas under pressure.

SUMMARY

In accordance with various embodiments, a surgical robotic access system is provided. The surgical robotic access system provides surgical robotic instruments and/or actuators access into a patient's body. In various embodiments, the surgical robotic access system comprises a surgical robotic access platform having a proximal portion disposed externally to a patient's body and a distal portion positioned within a patient's body. The proximal portion of the surgical robotic access platform includes a flexible seal. A robotic insertion tube has a proximal end disposed away from the proximal portion of the surgical robotic access platform and has a distal end embedded in the flexible seal of the surgical robotic access platform. The robotic insertion tube also has a lumen extending between the proximal end of the robotic insertion tube to the distal end of the robotic insertion tube through which a surgical robotic manipulator is insertable therethrough and through the flexible material.

In various embodiments, the surgical robotic access system comprises a sealing cap disposed externally to a patient's body in which the sealing cap includes a flexible seal. The surgical robotic access system also comprises a retractor with an outer ring removably connected to the sealing cap and an inner ring arranged to be positioned within the patient's body and a robotic insertion tube comprising an upper or outer access connector and a lower or inner access connector. The outer access connector is arranged to be removably coupled to a robotic sleeve and the inner access connector is embedded in the flexible seal of the sealing cap. The robotic insertion tube has a lumen extending through the outer access connector and the inner access connector and the flexible seal covering a portion of the lumen extending through the inner access connector and through which a surgical robotic manipulator insertable through the lumen is insertable through the flexible seal covering the portion of the lumen.

In various embodiments, the surgical robotic access system comprises a sealing cap disposed externally to a patient's body in which the sealing cap includes a flexible seal. The surgical robotic access system also comprises a robotic insertion tube comprising an outer access connector and an inner access connector. The outer access connector is arranged to be removably coupled to a robotic sleeve through which a robotic instrument is insertable therethrough and the inner access connector is embedded in the flexible seal of the sealing cap to permanently affix the inner access connector of the robotic insertion tube to the flexible seal. The flexible seal has a first region with a first thickness surrounding the robotic insertion tube and a second region having a second thickness disposed below the inner access connector of the robotic insertion tube. The first thickness of the flexible seal is greater than the second thickness of the flexible seal to provide a predetermined insertion force.

In various embodiments, the surgical robotic access system comprises a sealing cap disposed externally to a patient's body in which the sealing cap includes a flexible seal. The surgical robotic access system also comprises a robotic insertion tube comprising a first outer access connector and an inner access connector. The first outer access connector is removably coupled to a first robotic sleeve through which a first robotic manipulator is insertable therethrough and the inner access connector is embedded in the flexible seal of the sealing cap to permanently affix the robotic insertion tube to the flexible seal. A second outer access connector is removably coupled to a second robotic sleeve through which a first robotic manipulator is insertable therethrough. The first and second outer access connectors are arranged to be removably coupled to the inner access connector of the robotic insertion tube in that the first and second outer access connectors are interchangeable with the inner access connector.

Many of the attendant features of the present invention will be more readily appreciated as the same becomes better understood by reference to the foregoing and following description and considered in connection with the accompanying drawings in which like reference symbols designate like parts throughout.

DETAILED DESCRIPTION

In accordance with various embodiments, a surgical robotic access system provides access for surgical robotic manipulators that includes but is not limited to instruments, actuators and/or operative portions of a surgical robotic system. The robotic manipulators are robotically controlled by the surgical robotic system autonomously or through assistance of a surgeon without a surgeon in direct contact or physically grasping the surgical robotic manipulator. The surgical robotic access system provides for the introduction, operation and withdrawal of the surgical robotic manipulators into a body cavity without permitting the escape of pressurized fluid or gas. The surgical robotic access system also provides a multi-faceted range of movement without touching or effecting pressure on the opening in the patient. The surgical robotic access system in various embodiments provides laparoscopic or single site access, insufflation and/or smoke evacuation.

In accordance with various embodiments, as shown for example in FIGS. 1-29, the surgical robotic access system includes a surgical robotic access platform having a sealing cap 5 removably coupled to a retractor or protector 20. The sealing cap in various embodiments includes a robotic insertion tube 50. The robotic insertion tube provides access for surgical robotic manipulators, e.g., surgical robotic instruments or actuators. The sealing cap 5 comprises a flexible seal 15 that in various embodiments is made of a flexible material such as a gel material. The robotic insertion tube is embedded in flexible seal. By embedding the robotic insertion tube in the flexible seal, any forces that may dislodge the tube is eliminated or greatly reduced.

Figure 1:
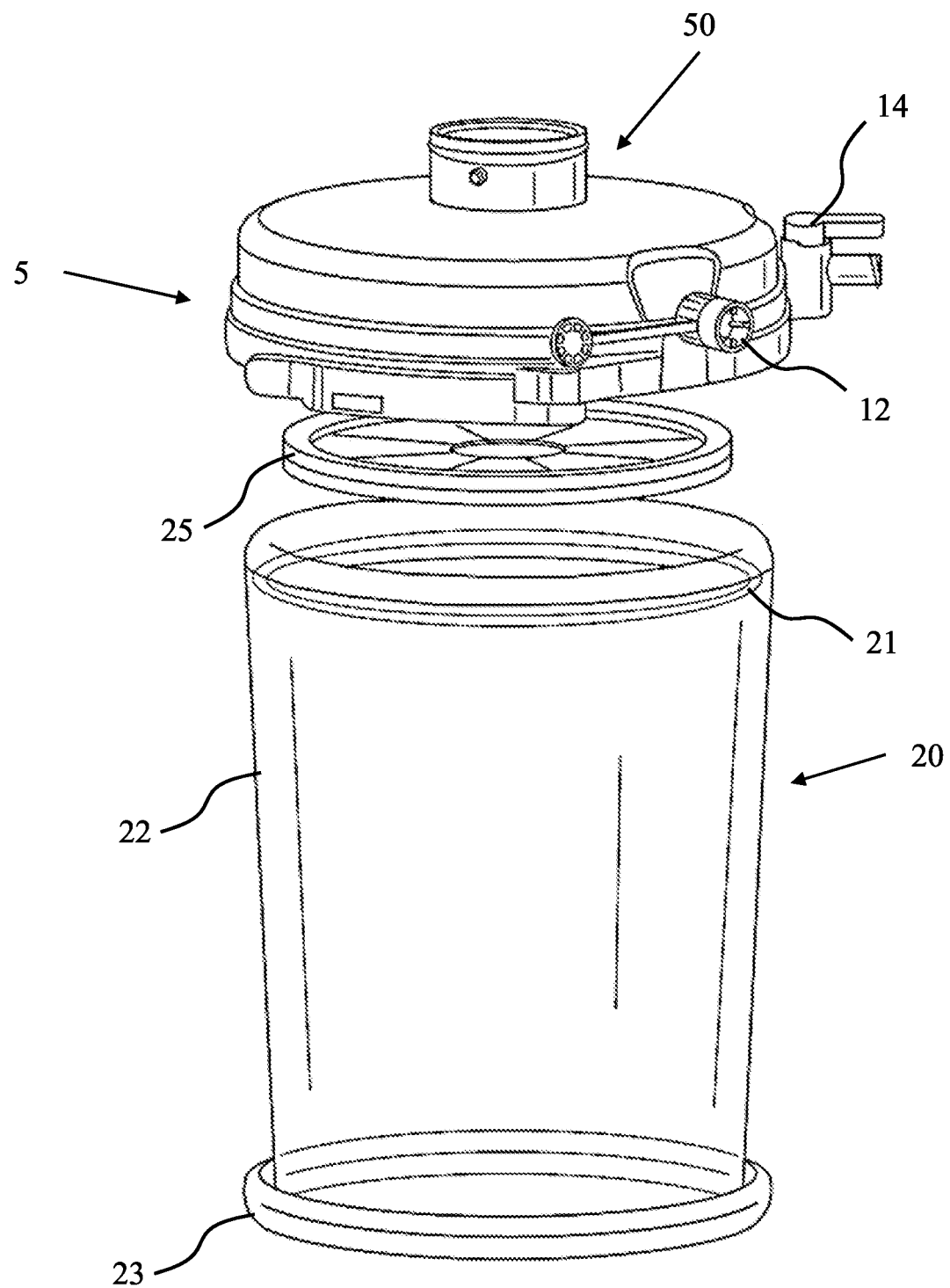
FIG. 1 is a disassembled view of a surgical robotic access system in accordance with various embodiments.
Figure 2:
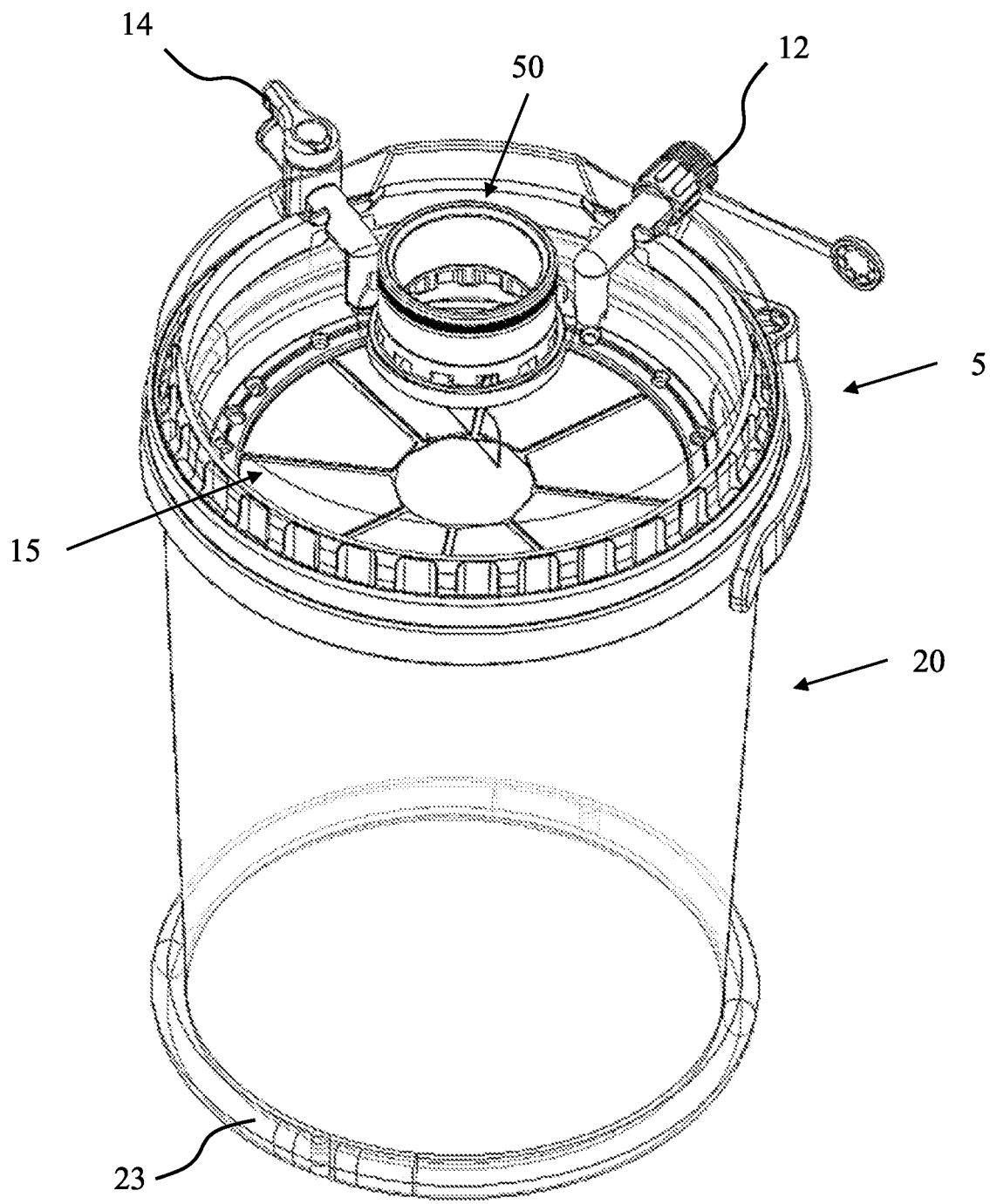
FIG. 2 is a perspective view of a surgical robotic access system in accordance with various embodiments with portions of the system shown transparent.
Figure 3:
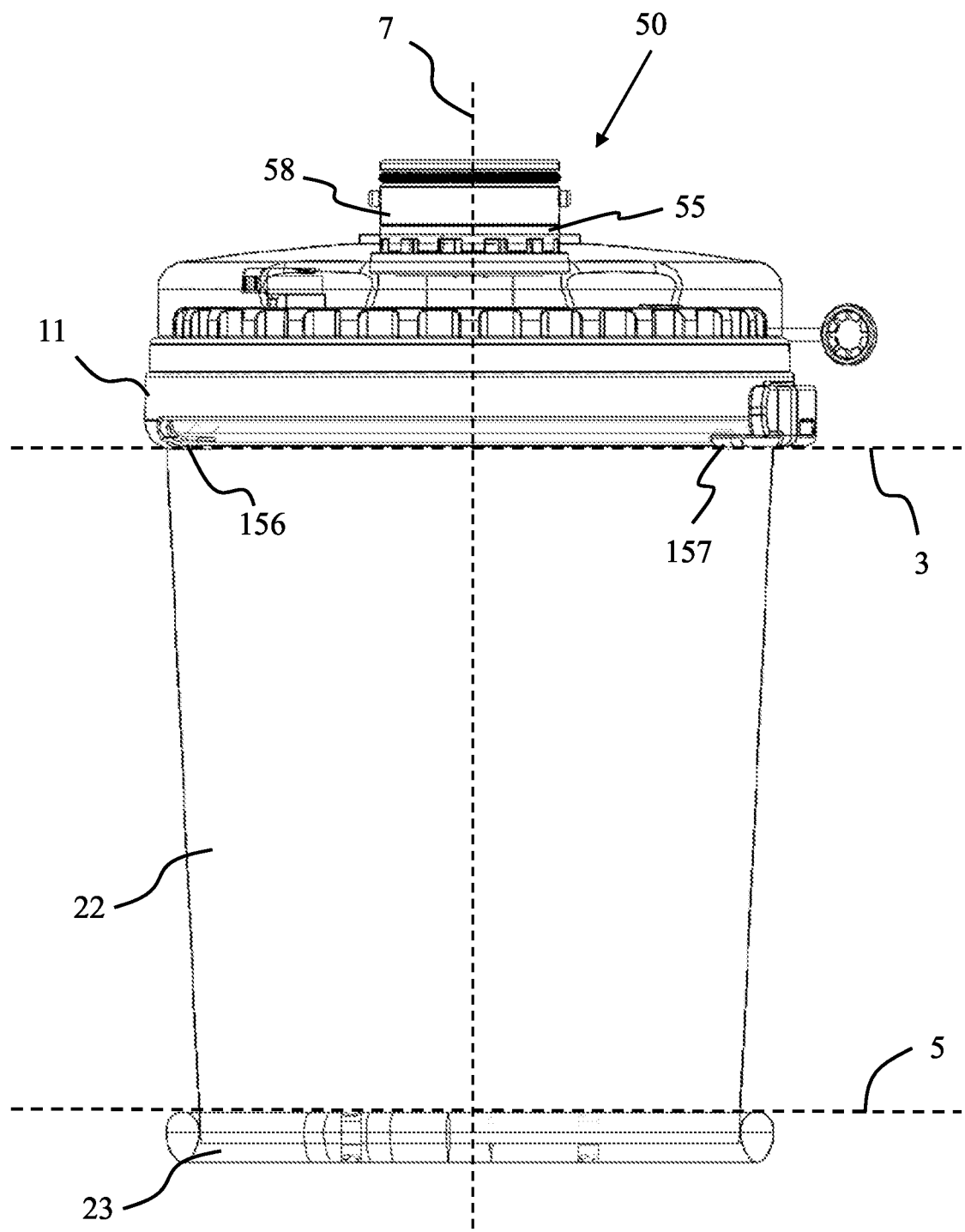
FIG. 3 is a side view of a surgical robotic access system in accordance with various embodiments with portions of the system shown transparent.
Figure 4:
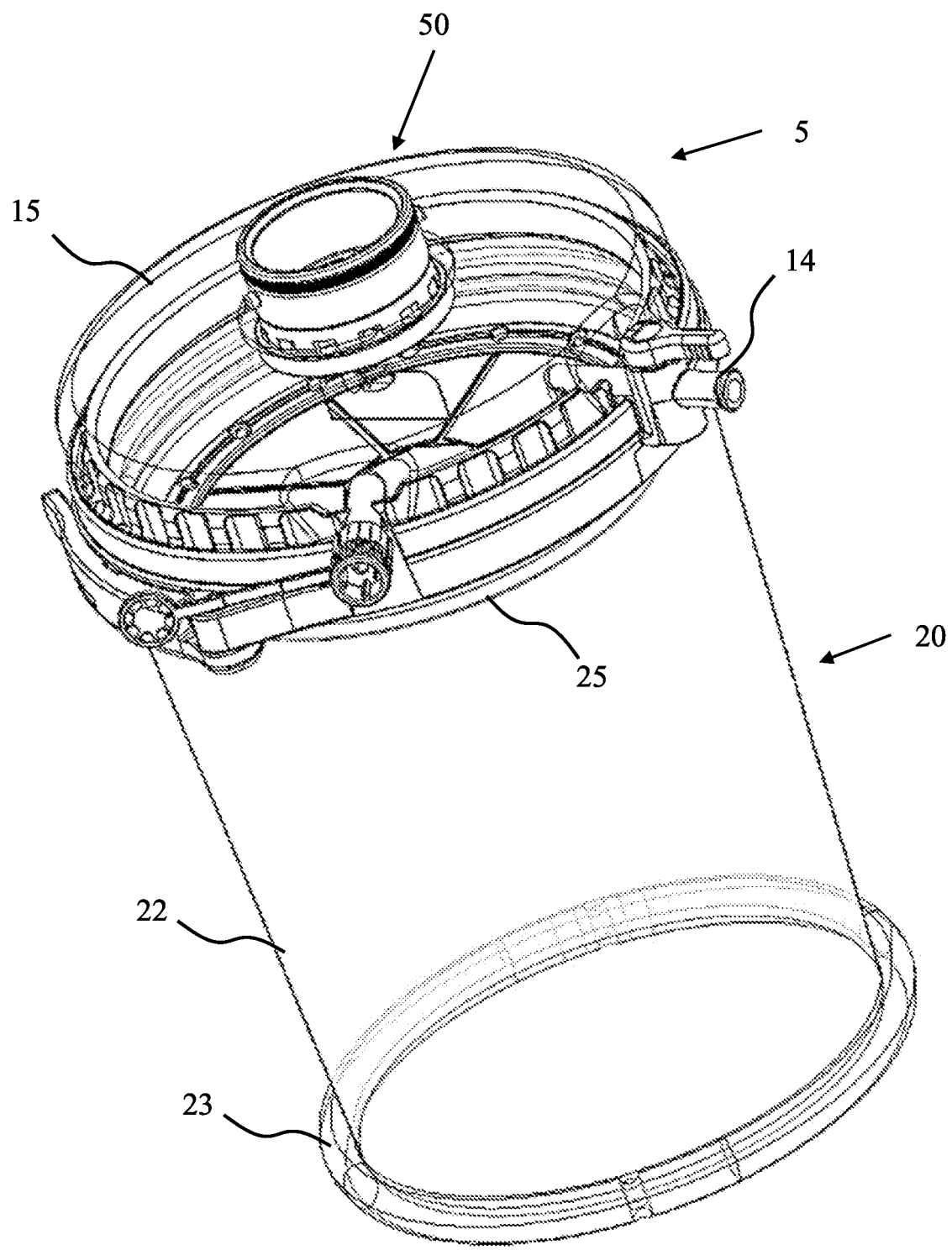
FIG. 4 is a perspective view of a surgical robotic access system in accordance with various embodiments with portions of the system shown transparent.
Figure 5:
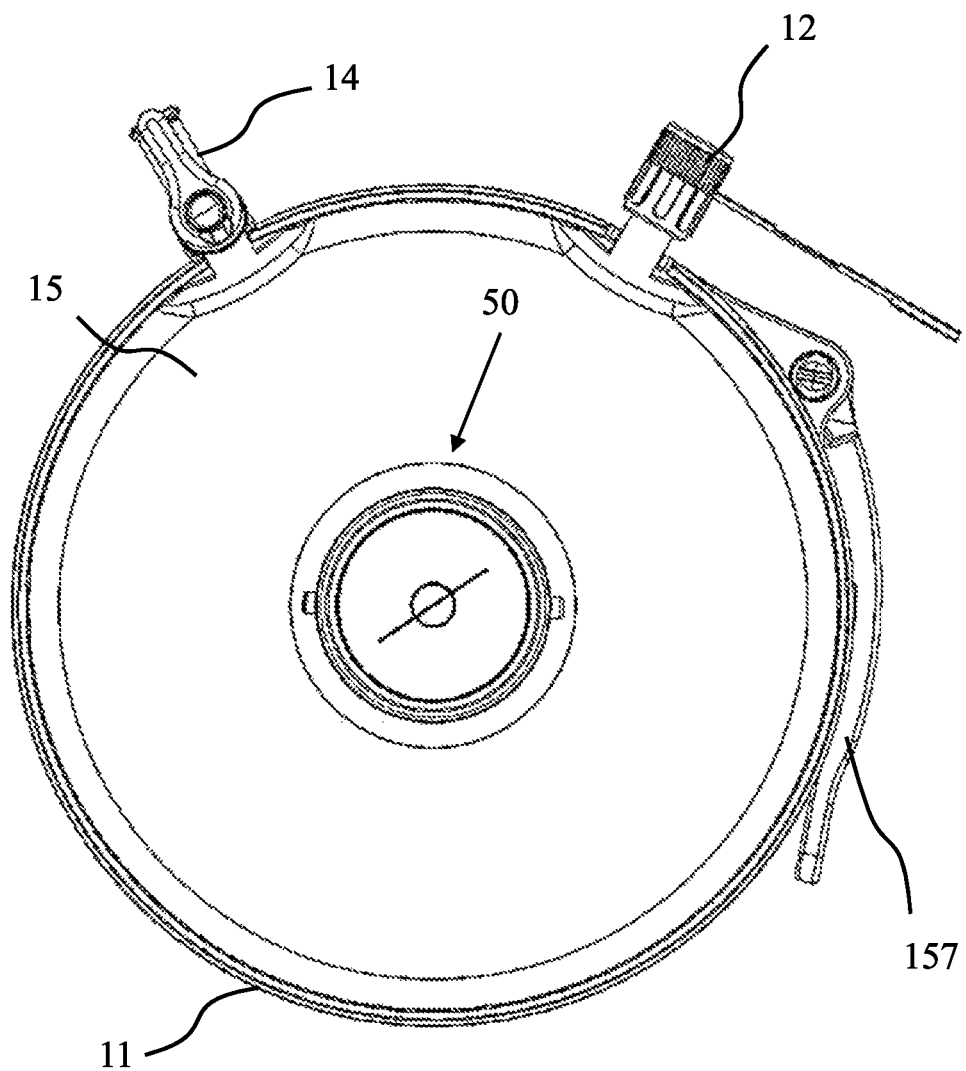
FIG. 5 is a top view of a surgical robotic access system in accordance with various embodiments.
Figure 6:
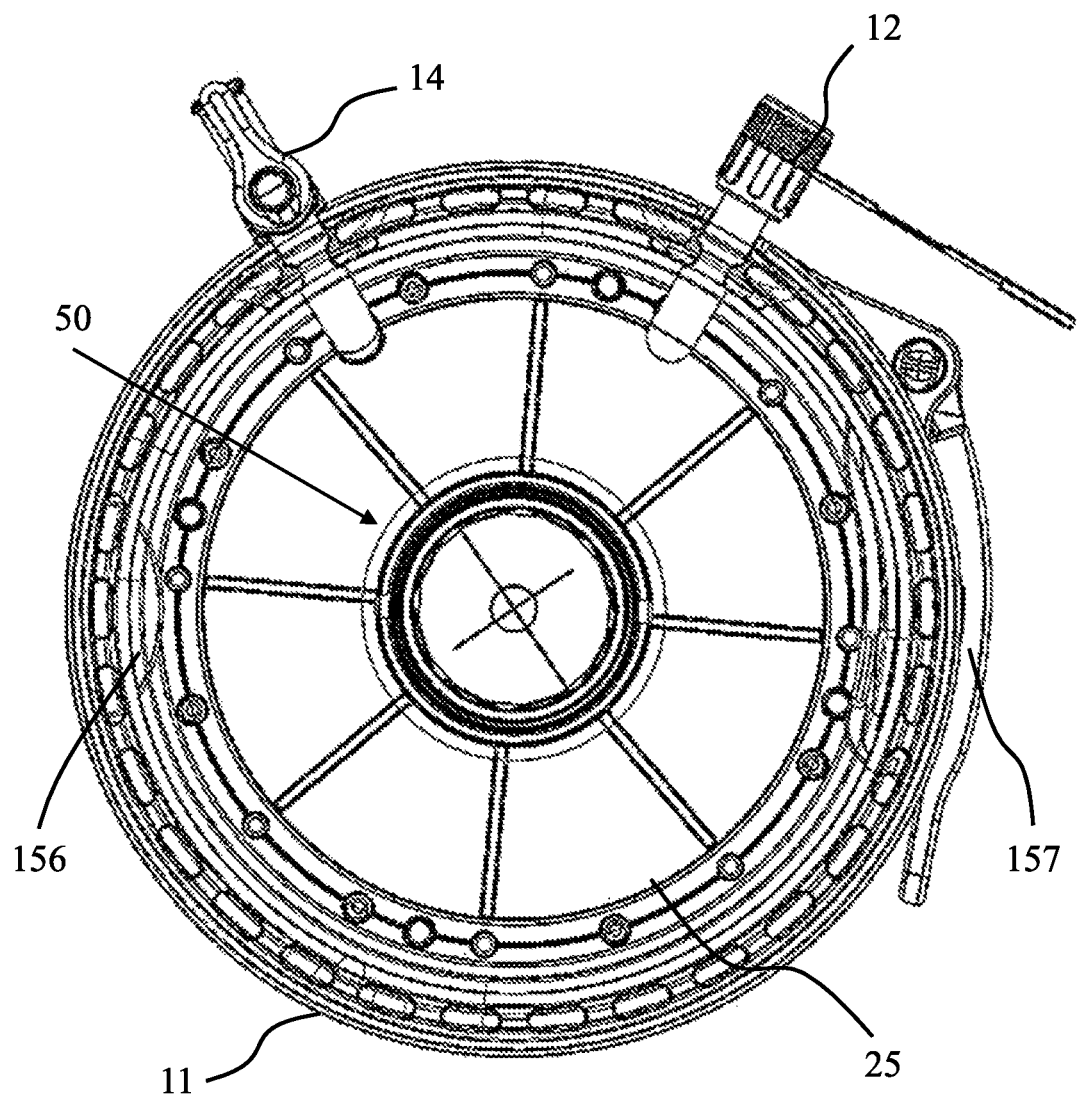
FIG. 6 is a top view of a surgical robotic access system in accordance with various embodiments with portions of the system shown transparent.
Figure 7:
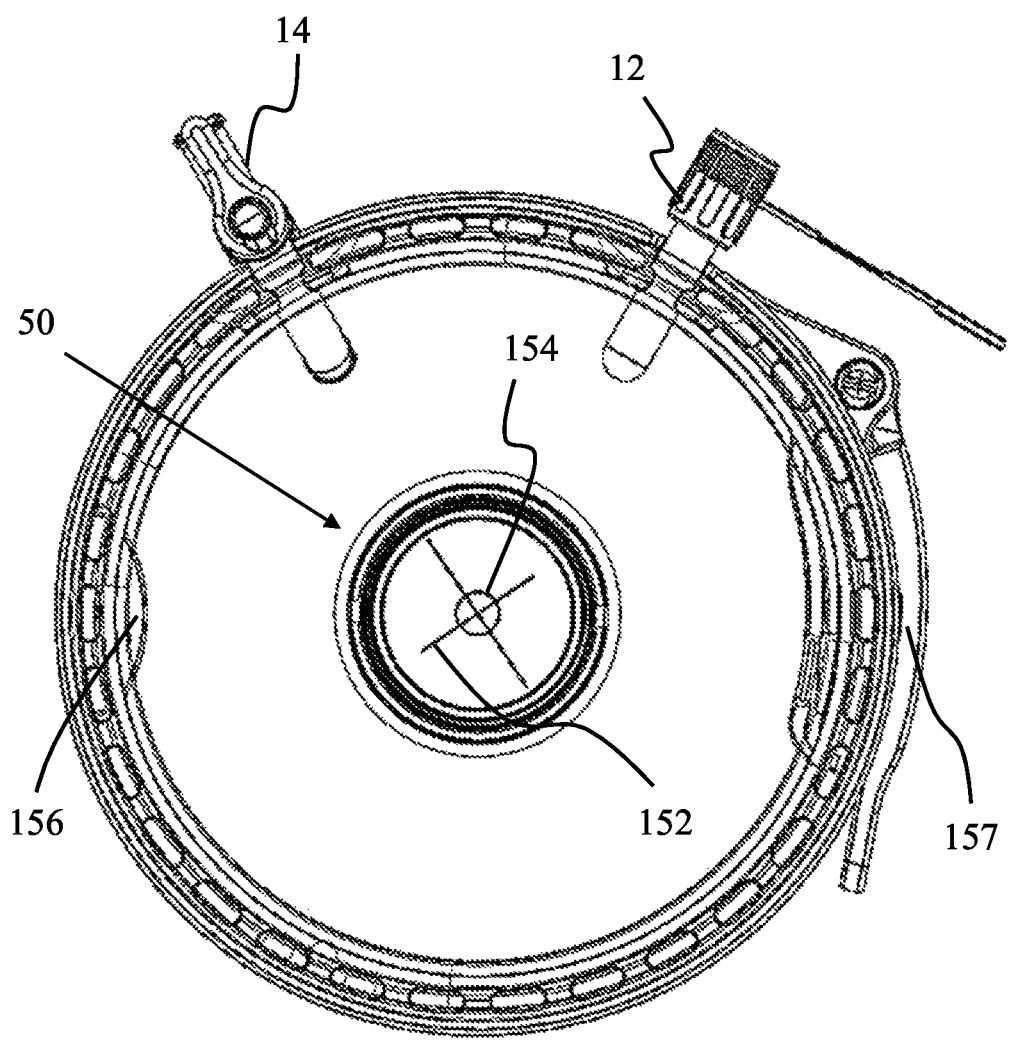
FIG. 7 is a top view of a surgical robotic access system in accordance with various embodiments with portions of the system shown transparent or removed.
Figure 8:
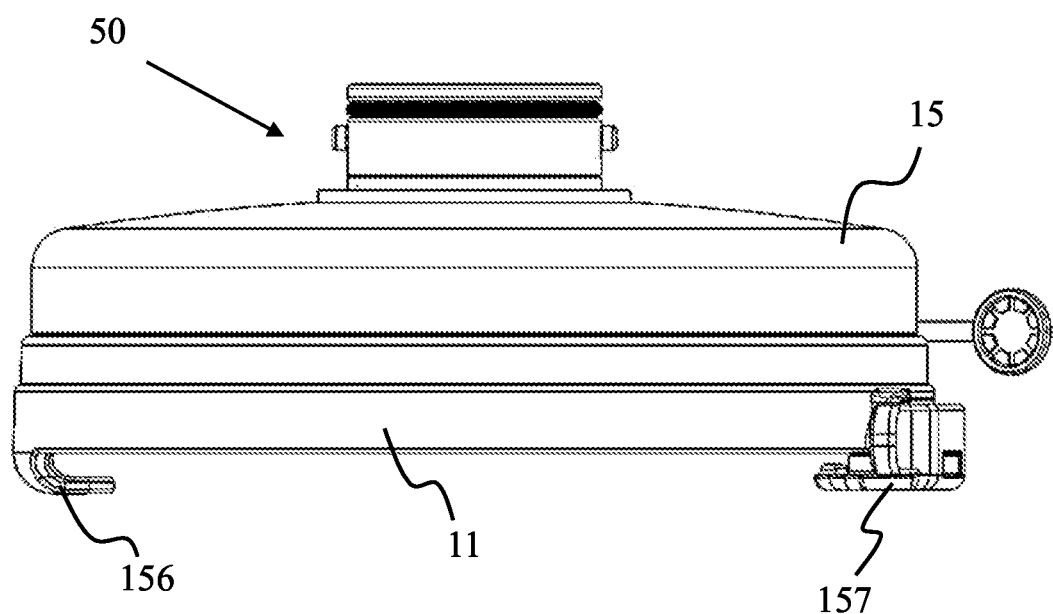
FIG. 8 is a side view of a sealing cap of a surgical robotic access system in accordance with various embodiments.
Figure 9:
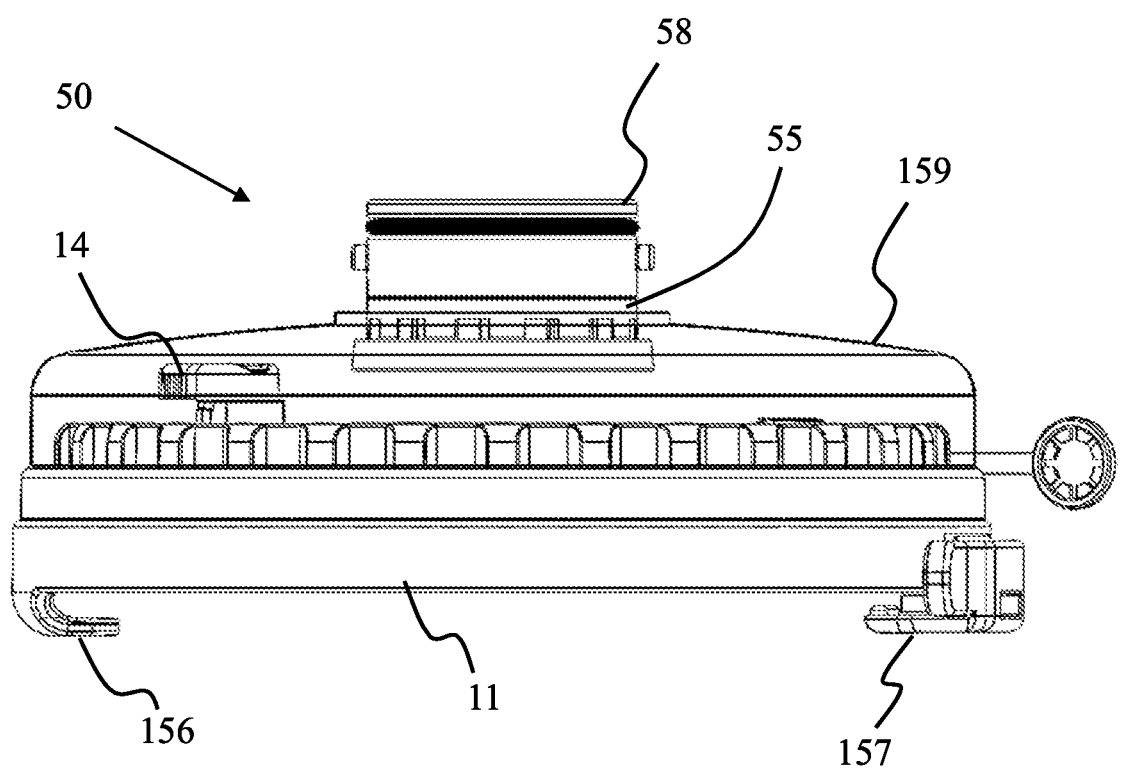
FIG. 9 is a side view of a sealing cap of a surgical robotic access system in accordance with various embodiments with portions of the system shown transparent.
Figure 10:
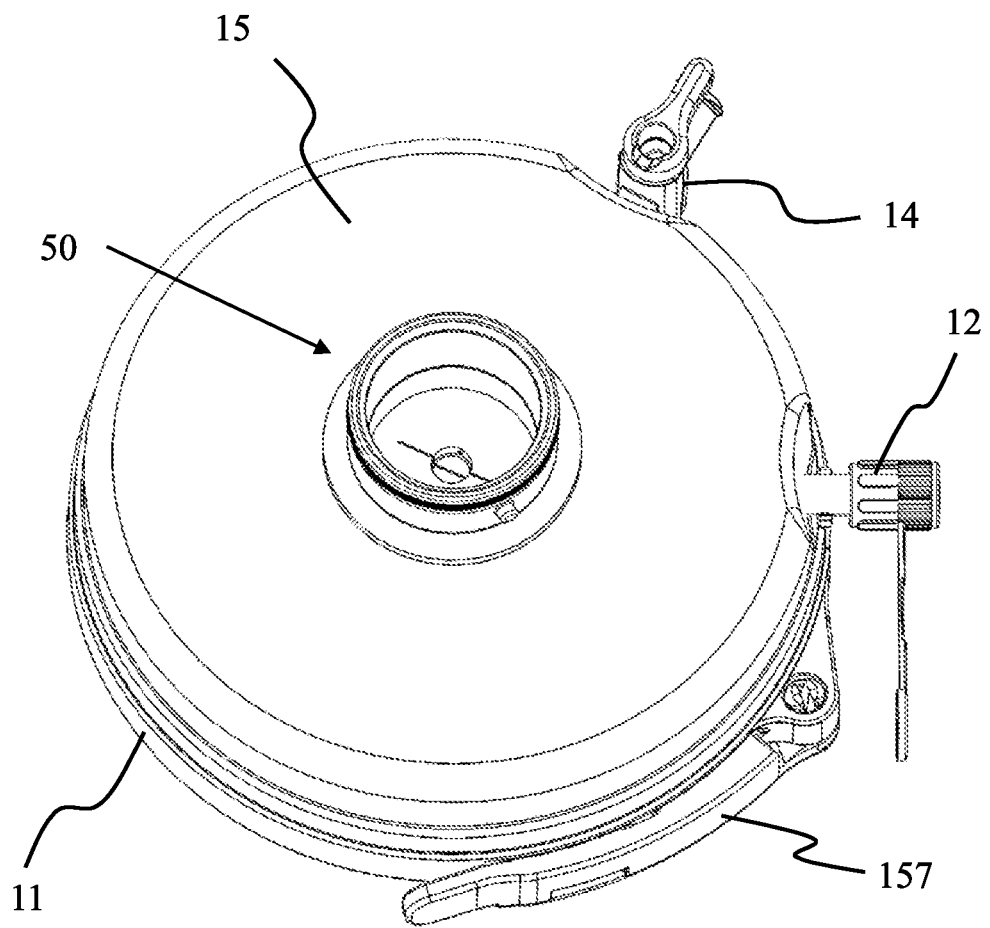
FIG. 10 is a perspective view of a sealing cap of a surgical robotic access system in accordance with various embodiments.
Figure 11:
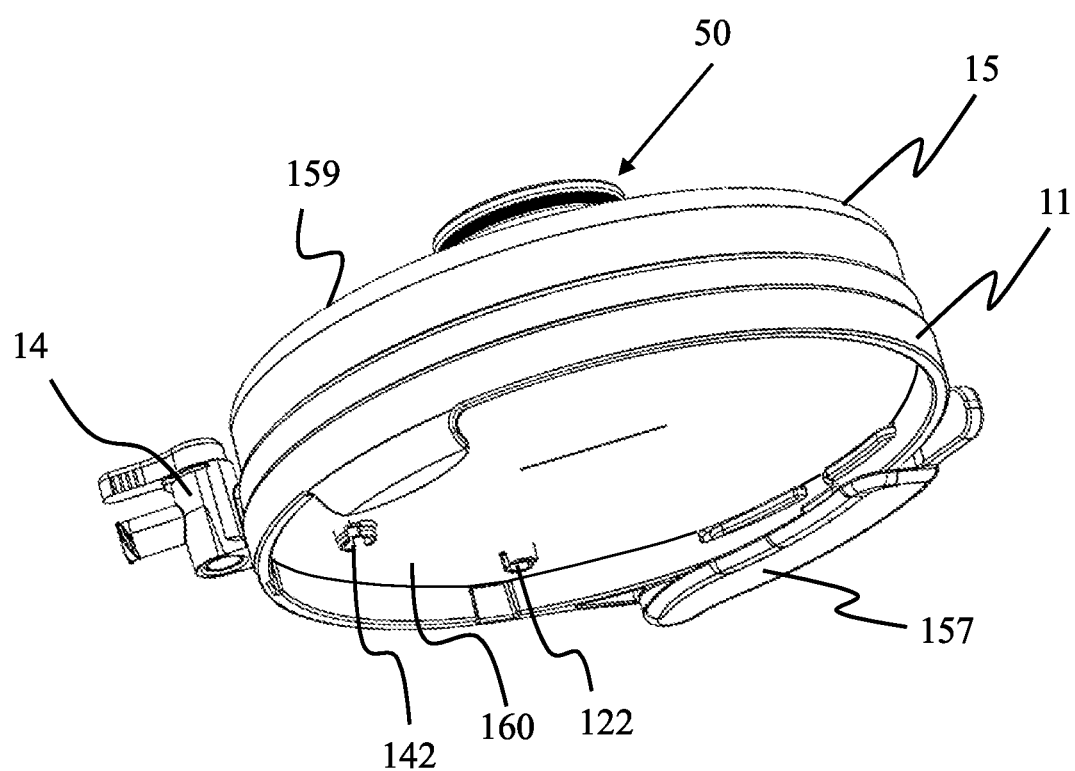
FIG. 11 is a perspective view of a sealing cap of a surgical robotic access system in accordance with various embodiments.
Figure 12:
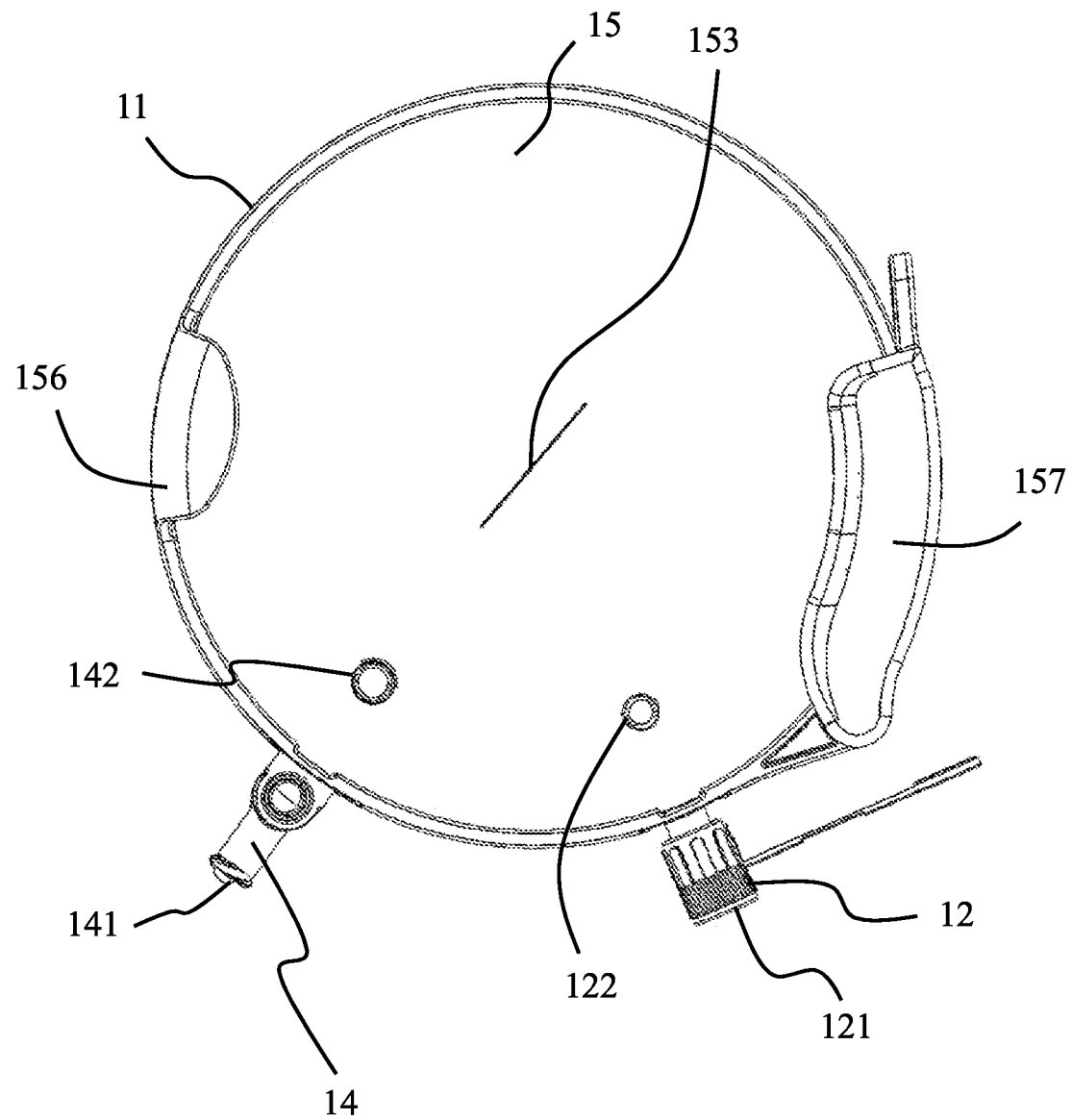
FIG. 12 is a bottom view of a sealing cap of a surgical robotic access system in accordance with various embodiments.
Figure 13:
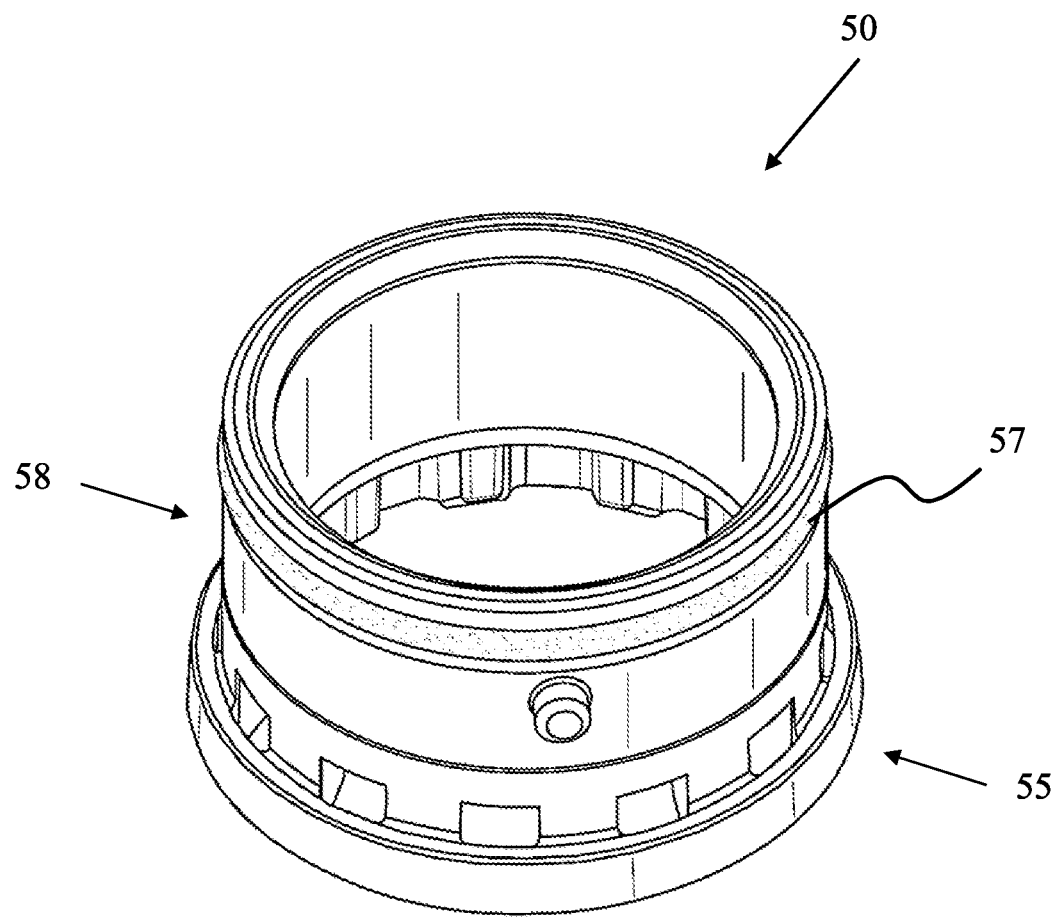
FIG. 13 is a perspective view of a robotic insertion tube of a surgical robotic access system in accordance with various embodiments.
Figure 14:
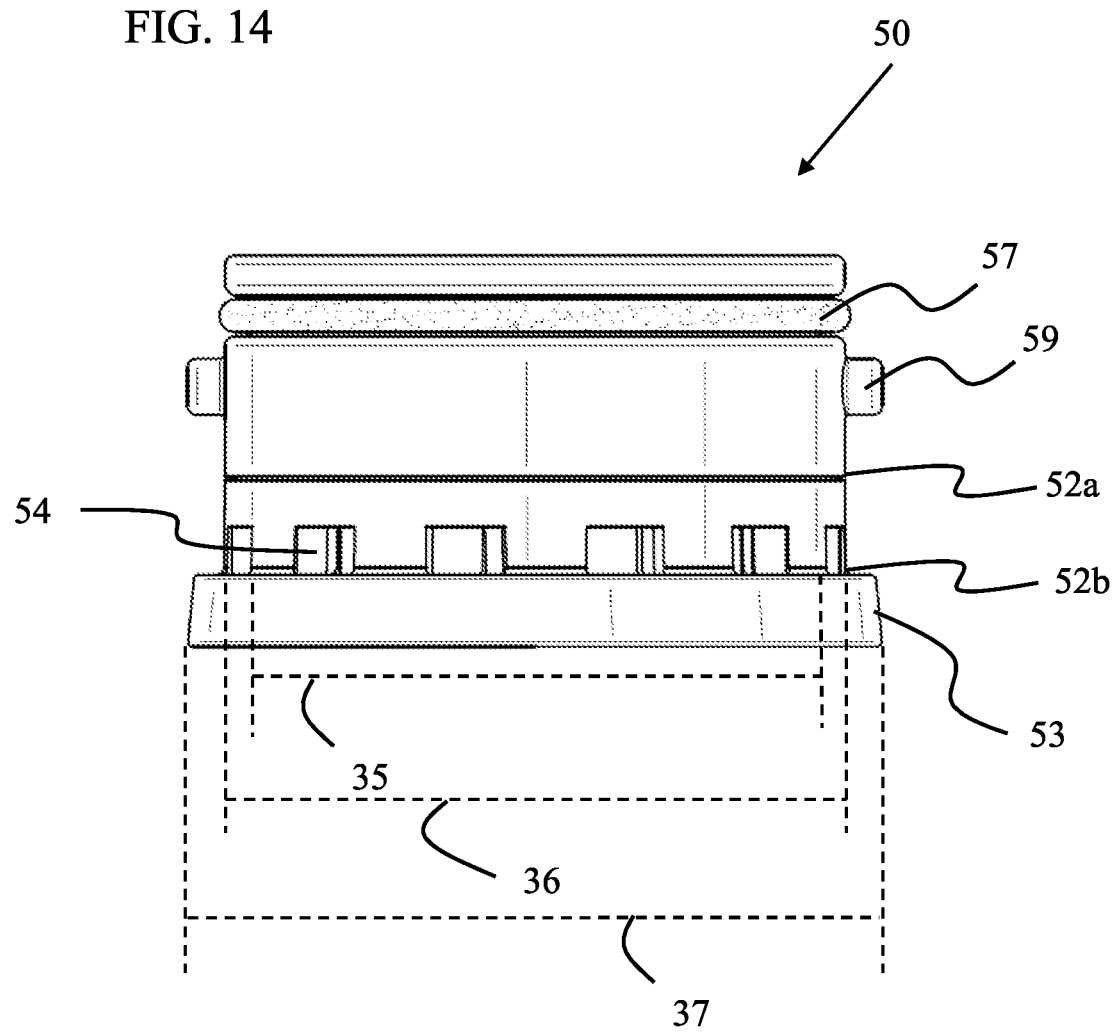
FIG. 14 is a side view of a robotic insertion tube of a surgical robotic access system in accordance with various embodiments.
Figure 15:
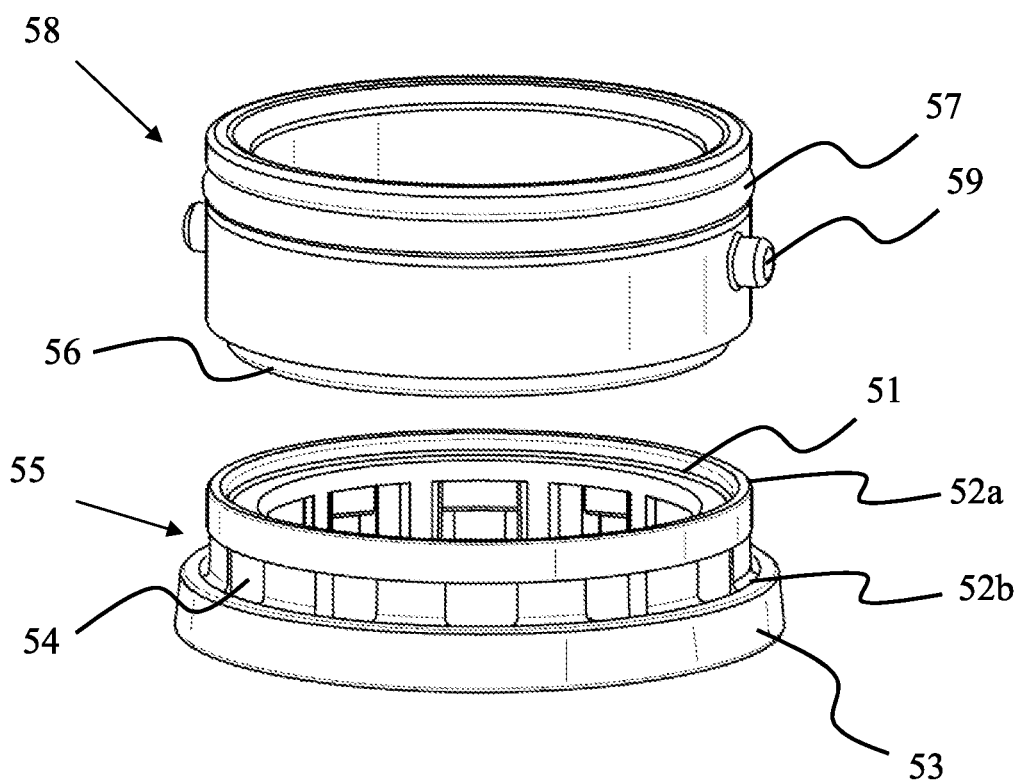
FIG. 15 is a perspective view of a robotic insertion tube of a surgical robotic access system in accordance with various embodiments.
Figure 16:
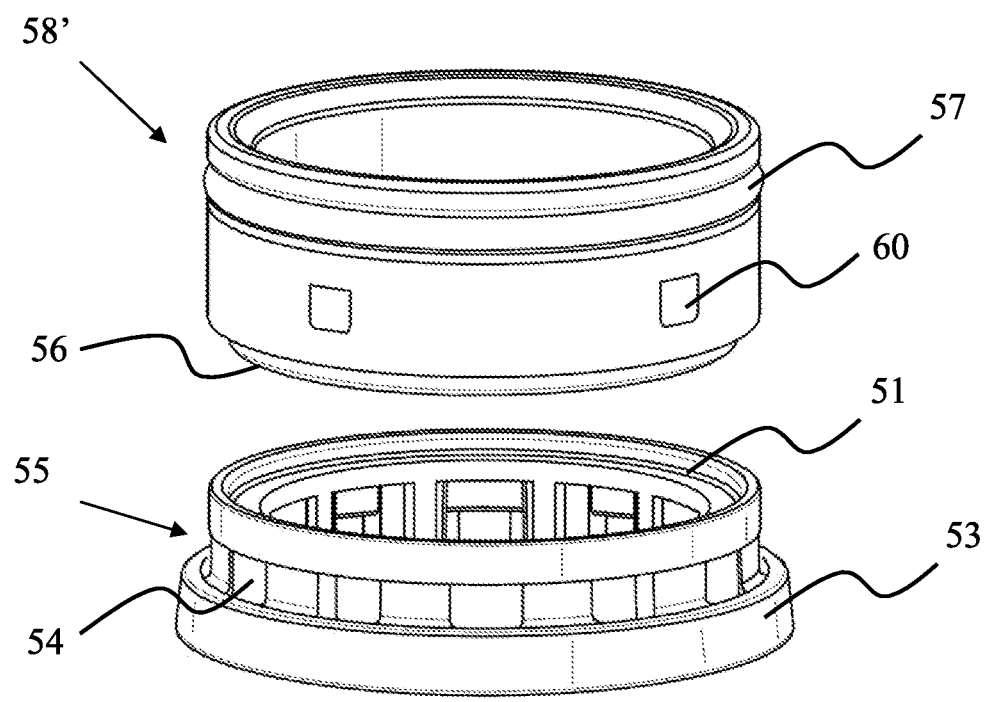
FIG. 16 is a perspective view of a robotic insertion tube of a surgical robotic access system in accordance with various embodiments.

As shown, for example, in FIGS. 14-16, the robotic insertion tube 50 includes an inner access connector 55 and an outer access connector 58. In various embodiments, the inner access connector is embedded in the flexible seal 15. In various embodiments, the inner access connector is tubular or cylindrical extending from a proximal end 52a to a distal end 52b and connects to or extends into a distal flange or base 53. Within the distal base or at the distal end of the inner access connector are a plurality of apertures 54 that provide access points or anchors to allow the flexible seal 15 to attach and hold the distal base and the distal end of the inner access connector in place and embedded in the flexible seal. The flexibility or resiliency of the flexible seal however allows the inner access connector 55 to float, pivot or move in various directions unhindered but limited within the inner diameter or area delimited by the sealing cap 5. However, the inner access connector is embedded or otherwise fixed within or irremovable from the flexible seal and thus cannot be removed or dislodged from the flexible seal.

The inner access connector 55 in various embodiments extends only partially through the flexible seal. As such, the flexible seal 15 of the sealing cap is disposed below or under portions of the inner access connector. The inner access connector defines or delimits an access passageway or lumen with an inner diameter 35 through which a robotics manipulator can extend there through and through the flexible seal. The flexible seal provides an instrument seal around or sealingly engages the outer surface of the inserted robotic manipulator as the manipulator is inserted, utilized or withdrawn from the inner access connector. The flexible seal also provides a zero seal in various embodiments in the absence of a robotic manipulator inserted in or through the inner access connector. Such seals prevent an escape of gas or fluids. In various embodiments, as shown for example in FIG. 14, the inner access connector defines an outer diameter 36 that is greater than the defined inner diameter 35. The outer diameter 36 is similar to or equal to the outer diameter of the outer access connector 58. Similarly, the inner diameter 35 of the inner access connector is similar to or equal to the inner diameter of the outer access connector. The distal base 53 of the inner access connector also defines a secondary or maximum outer diameter 37 that is greater than the outer diameter 36 to further assist in the securement of the inner access connector to the flexible seal.

Figure 17:
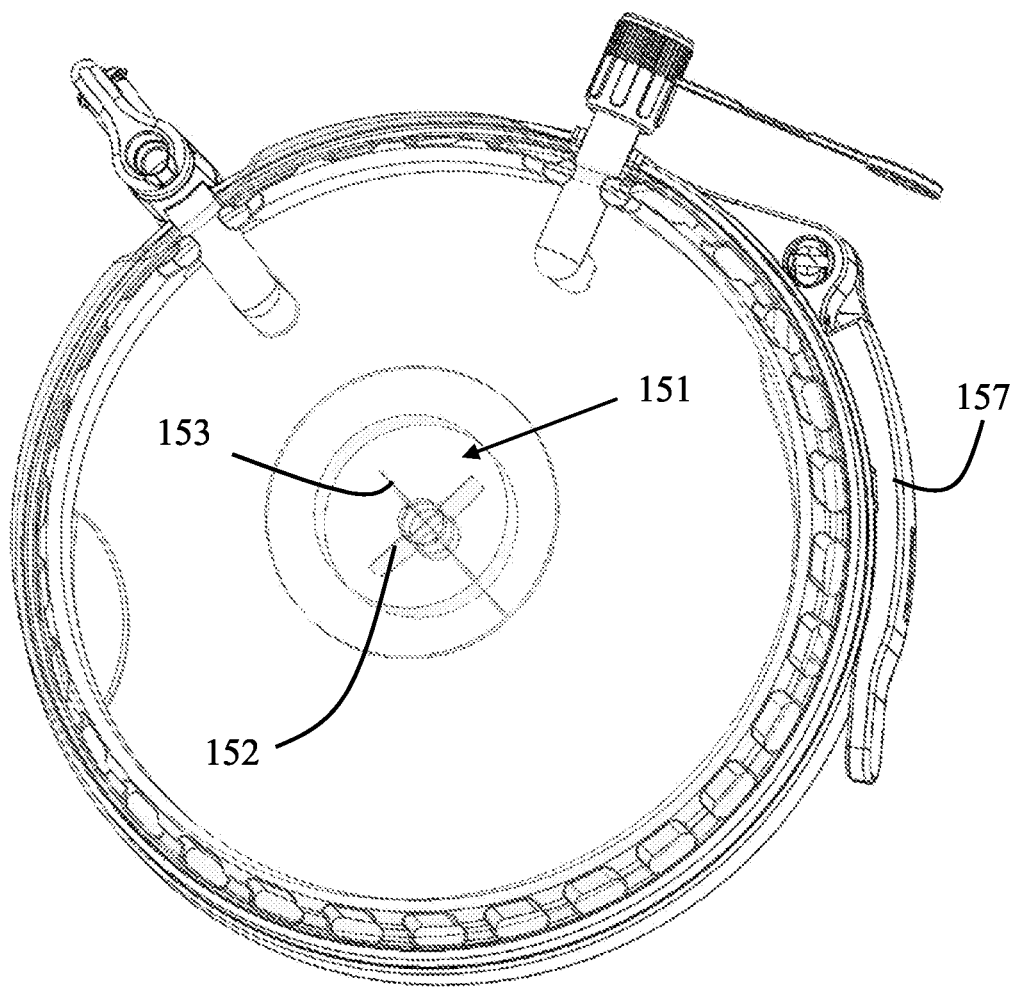
FIG. 17 is a perspective view of a sealing cap of a surgical robotic access system in accordance with various embodiments with portions of the sealing cap shown transparent or removed.
Figure 18:
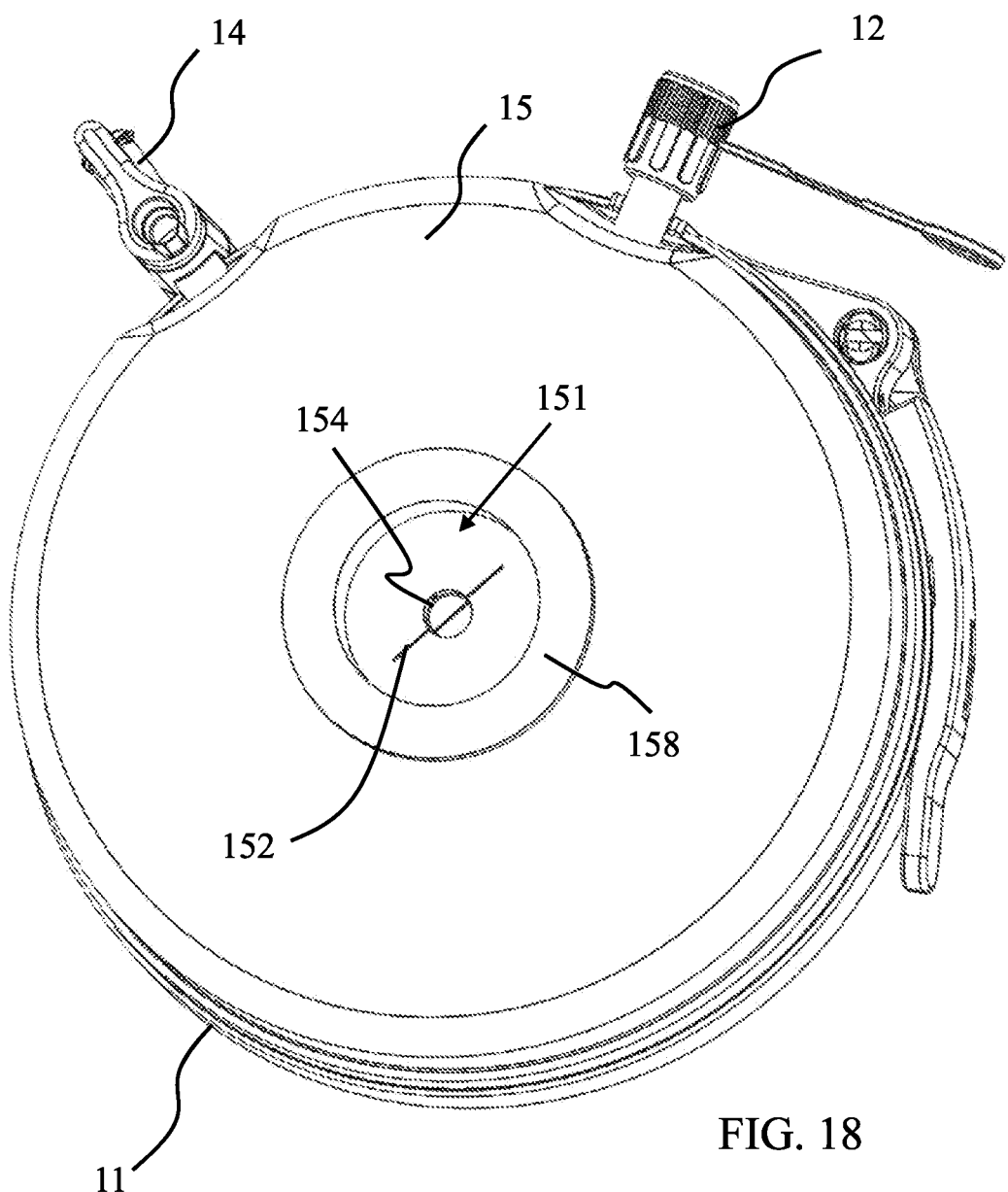
FIG. 18 is a perspective view of a sealing cap of a surgical robotic access system in accordance with various embodiments with portions of the sealing cap removed.
Figure 19:
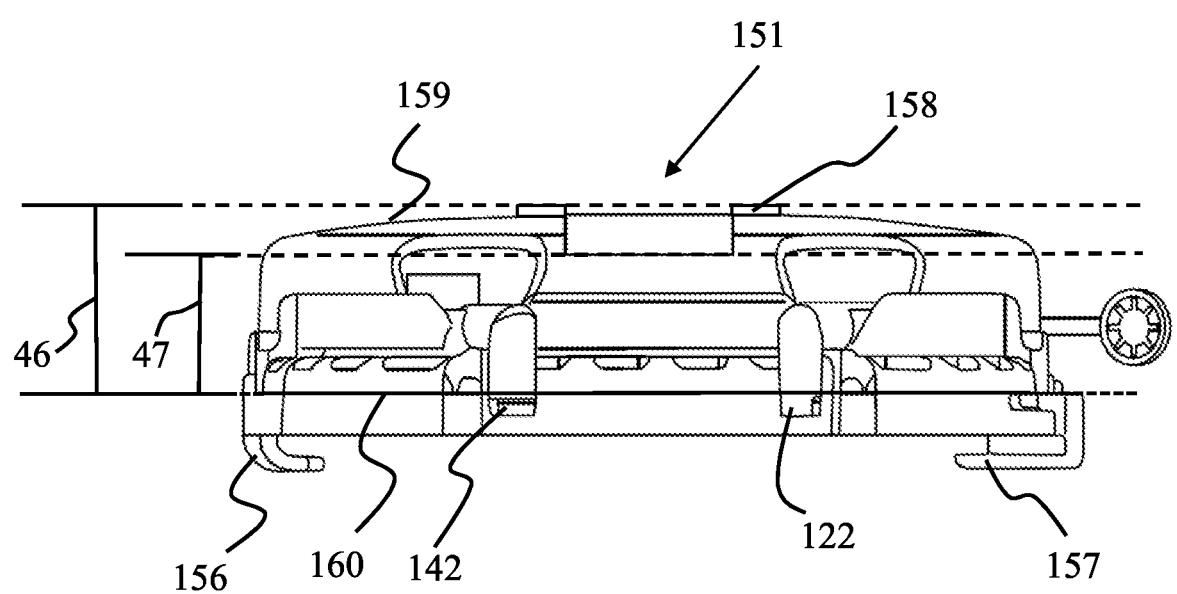
FIG. 19 is a cross-sectional view of a sealing cap of a surgical robotic access system in accordance with various embodiments with portions of the sealing cap removed.
Figure 20:
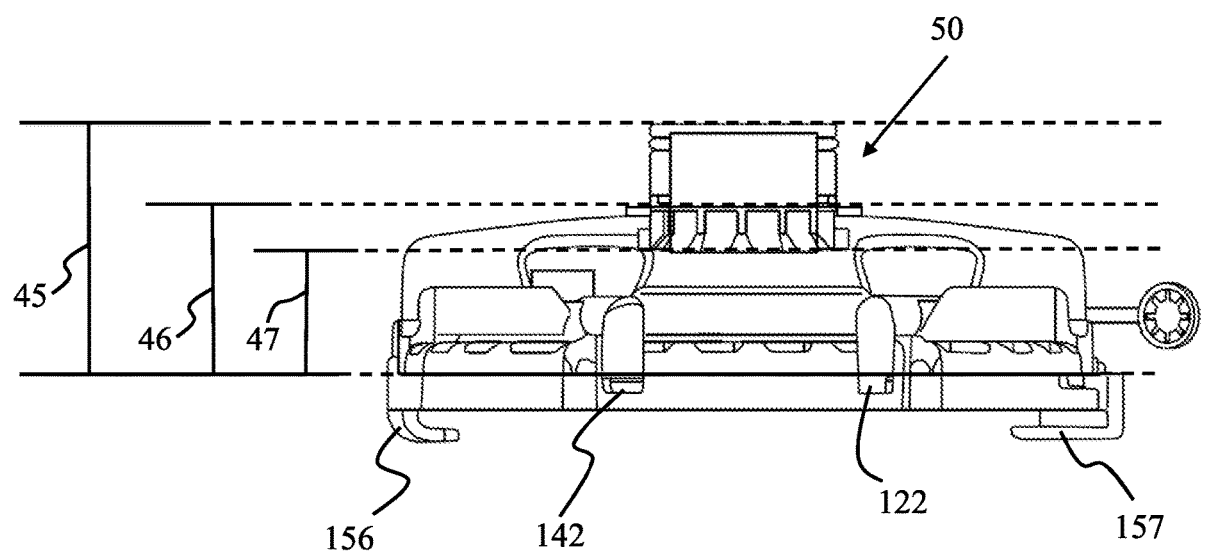
FIG. 20 is a cross-sectional view of a sealing cap of a surgical robotic access system in accordance with various embodiments.

In various embodiments, as shown for example in FIGS. 17-19, the flexible seal has a cavity 151 disposed between the inner periphery of the inner access connector of the robotic insertion tube. As such, in various embodiments, the flexible seal has a predetermined or predefined maximum height 46 and where the inner access connector is embedded in the flexible seal, the flexible seal has a reduced height 47 relative to the surrounding flexible seal. This cavity or reduced portion of the flexible seal (e.g., reduced height, area or volume of flexible seal) is within and where the inner access connector is attached thereto. As such, the diameter or width of the cavity 151 is equal to the outer diameter 36 of the inner access connector. Also, the maximum diameter or width of the entire flexible seal is significantly greater than the diameter or width of the cavity 151. The cavity provides an area or free region or space for the flexible seal to displace as a surgical robotic manipulator is inserted there through and thereby easing or reducing insertion force. The displacement area however is also limited or confined by the inner periphery of the inner access connector and thus biases or causes the flexible seal to tend to seal against the inserted surgical robotic manipulator. The cavity also provides limited displacement of the flexible seal when pressurized from gases within the body cavity to further enhance the seal with or without a manipulator inserted there through.

The flexible seal disposed below the robotic insertion tube, e.g., the reduced portion of flexible includes a slit 152 to assist in insertion of a manipulator and sealing against the manipulator or in the absence of the manipulator. In various embodiments, the slit 152 is a single slit or a plurality of slits with one slit 153 orthogonal or angled from another slit 152 and positioned deeper or lower within the flexible seal than the other slit 152. The reduced portion of flexible seal also limits and thus predefines the amount of material the surgical robotic manipulator will encounter upon contact and insertion. With this predefined and constant amount, the forces needed by a surgical robotic manipulator to be inserted into and through the flexible seal can be predefined or determined to provide haptic or tactile feedback to the surgical robotic system to consistently identify when a surgical robotic manipulator has been inserted initially, partially and completely into the flexible seal, through the flexible seal or withdrawn from the flexible seal despite the geometry of the tips or distal end of the manipulator. In various embodiments, the distance or height 45 from the top or proximal end of the robotic insertion tube 50 to the inner surface 160 of the flexible seal 15 is greater than the maximum height 46 of the flexible seal 15. In various embodiments, the surgical robotic system includes a robotic sleeve surrounding and/or sealing or protecting the robotic manipulator. As such, this distance or height or difference in distance or height increases access for the robotic sleeve and enhances coupling of the robotic sleeve and freedom of movement of the robotic sleeve and the robotic insertion tube embedded in the flexible seal 15.

In various embodiments, the inner access connector has a distal or inner end 53 embedded in the flexible seal 15 and a proximal or outer end 52 that is not embedded in the flexible seal and thus is disposed outside, proximate or above the outer surface 159 of the flexible seal. The distal end of the inner access connector does not extend through the flexible seal and thus is disposed above or doesn't extend pass or through the inner surface 160 of the flexible seal. The flexible seal seals the opening through the inner access connector and the plurality of apertures around the inner access connector.

The flexible seal in various embodiments, as shown for example in FIGS. 1-12, is contained or attached to a ring 11 and in various embodiments an insufflation port 14, an evacuation port 12 or both are disposed there through and through the flexible seal to access the body cavity. As such, gas or fluid such as insufflation gas can be externally supplied via an inlet 141 of the insufflation port 14 from a gas source outside or external to the patient and the surgical robotic access system into the patient through an outlet 142 of the insufflation port while the flexible seal prevents any gas or fluid from escaping. Similarly, gas or fluid such as smoke may be extracted from within the patient through the inlet 122 of the evacuation port 12 and pulled out externally through an outlet 121 of the evacuation port 12 into an appropriate canister, suction or evacuation system to properly dispose of the potentially harmful or disruptive gas or fluid. In various embodiments, an outer portion or periphery of the flexible seal is coupled to the ring 11 and in one embodiment is molded to a plurality of apertures disposed along the periphery of the ring. In various embodiments, the ring 11 of the sealing cap includes a pivotably coupled latch 157 along with a stationary ledge or flange 156 to assist in removably coupling the sealing cap to the protector. In various embodiments, the ring and flexible seal are made of the same material and thus together form a monolithic structure.

In the illustrated embodiment, a raised portion 158 of the flexible seal surrounds the cavity 151 to further secure or reinforce the attachment of the robotic insertion tube to the flexible seal. In various embodiments, the raised portion is removed to provide the flexible seal a uniform height or thickness throughout the seal. In various embodiments, a center cavity 154 is disposed within the cavity 151 to further assist in the insertion of a manipulator and sealing against the manipulator or in the absence of the manipulator. As such, the center cavity provides another reduced layer of thickness or increased flexibility relative to the surrounding cavity 151 and the surrounding flexible seal, e.g., the raised portion of flexible seal or the material within the cavity or between the cavity and the edge or outer periphery of the sealing cap.

In various embodiments, the inner and outer access connectors 55, 58 of the robotic insertion tube 50 are separate components. In various embodiments the inner access connector remains fixed and unchanged while the outer access connector may be disconnected and replaced or interchanged with another outer access connector with a different robotic coupling interface. As such, in various embodiments, the inner access connector and the outer access connector include mating connections 51, 56 such as threading, snaps or the like to removably couple the outer and inner access connectors together. Accordingly, the outer access connector can be interchanged with other outer access connectors that provide the associated connection particular for a specific robotic manipulator and/or sleeve. For example, FIG. 16 illustrates an outer access connector 58' similar to the outer access connector 58 but having apertures 60 to releasably connect to tabs or detents of a different robotic coupling interface of a different robotic sleeve. The apertures 60 do not extend into the lumen of the outer access connector thereby maintaining the seal integrity within the robotic insertion tube. Other portions of the outer access connector may also vary such as the seal on it outer surface along with different sizes and shapes to accommodate the varied coupling interface for other robotic sleeves. The different or varied robotic sleeves may be used for or to identify different robotic manipulators or other identifying indicia of the robotic manipulator operation, surgical robotic system or surgical procedure.

In cases where the outer access connector is permanently affixed to or not otherwise removable from the inner access connector to enhance stability of the robotic insertion tube, to interchange different outer access connectors or in particular different robotic coupling interfaces of the outer access connectors to accommodate different robotic sleeves, the entire sealing cap is replaceable with a different sealing cap. As such, a first sealing cap can include an inner access connector embedded in the flexible seal of the sealing cap with an outer access connector affixed to the inner access connector and a separate second sealing cap can include an inner access connector embedded in the flexible seal of the sealing cap with an outer access connector affixed to the inner access connector with this outer access connector having a different or specialized robotic coupling interface relative to the other robotic coupling interface of the outer access connector of the first sealing cap. As such, the first sealing cap can be interchanged with the second sealing cap as required for the corresponding needed robotic coupling interface. This can also be the case for access connectors that can be separated to provide alternative connections or quick changes if desired or required by the particular surgical or robotic system or procedure.

Figure 21:
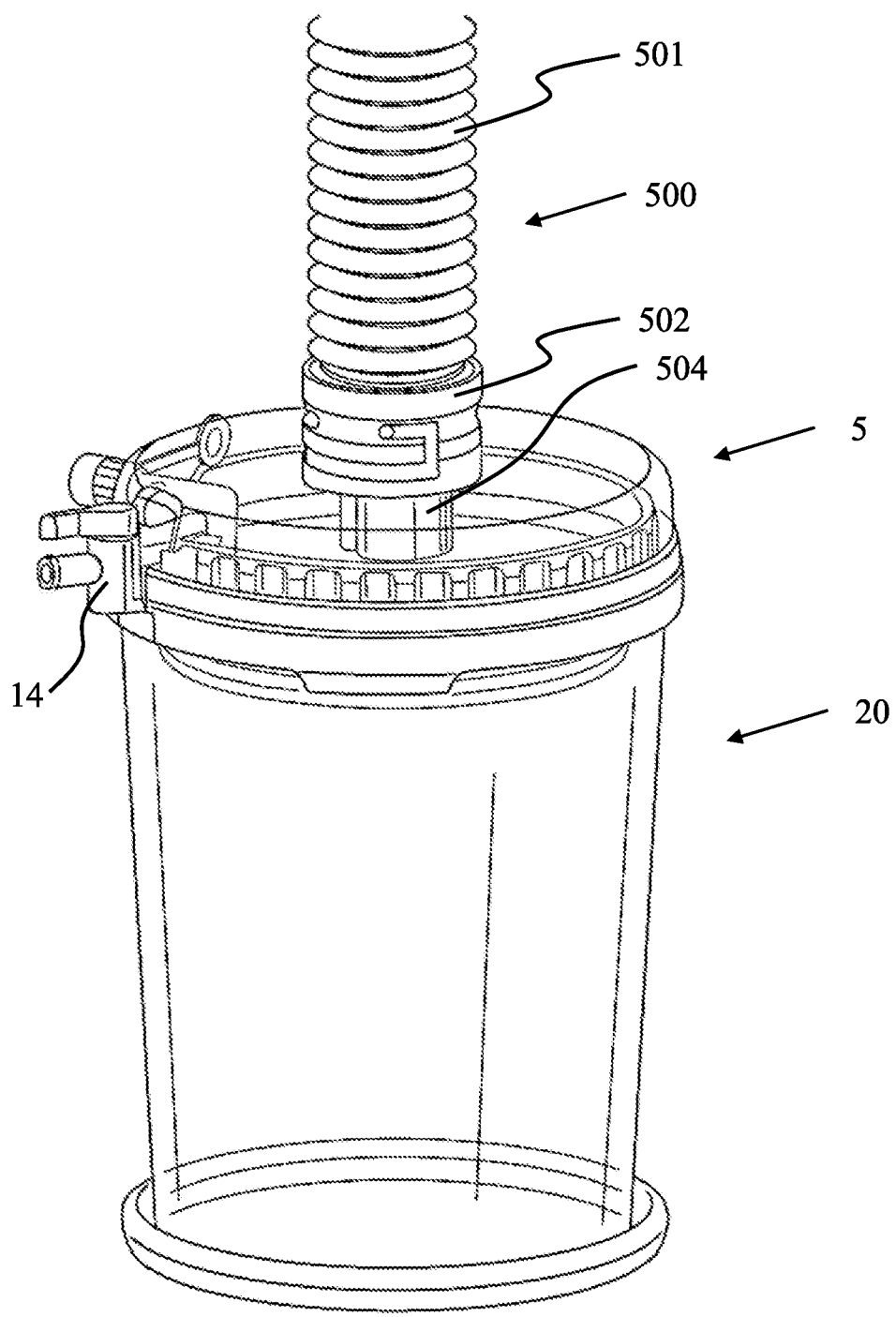
FIG. 21 is a perspective view of a surgical robotic access system in accordance with various embodiments with a robotic sleeve connected thereto and with portions of the sealing cap shown transparent.
Figure 22:
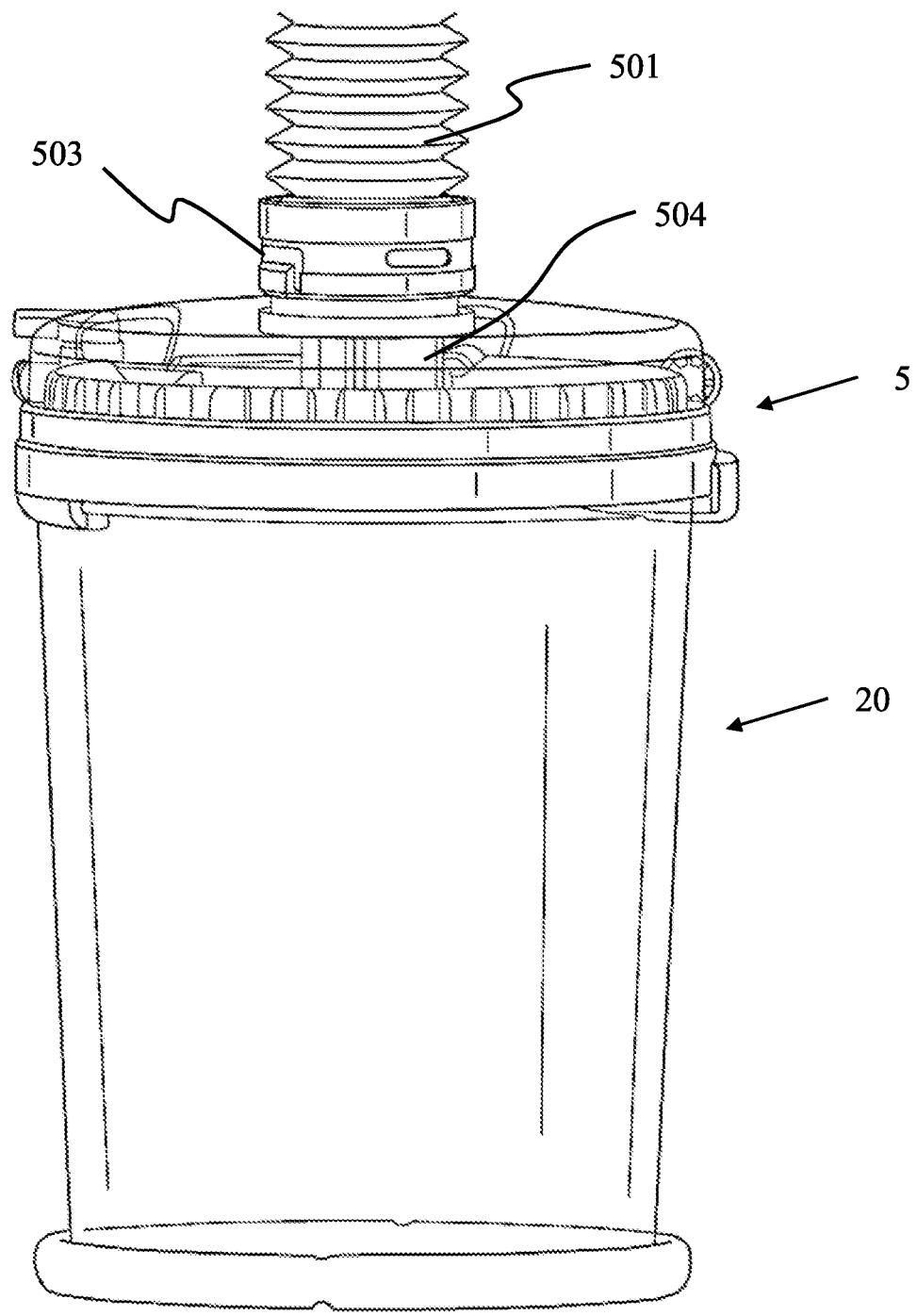
FIG. 22 is a perspective view of a surgical robotic access system in accordance with various embodiments with a robotic sleeve connected thereto and with portions of the sealing cap shown transparent.
Figure 23:
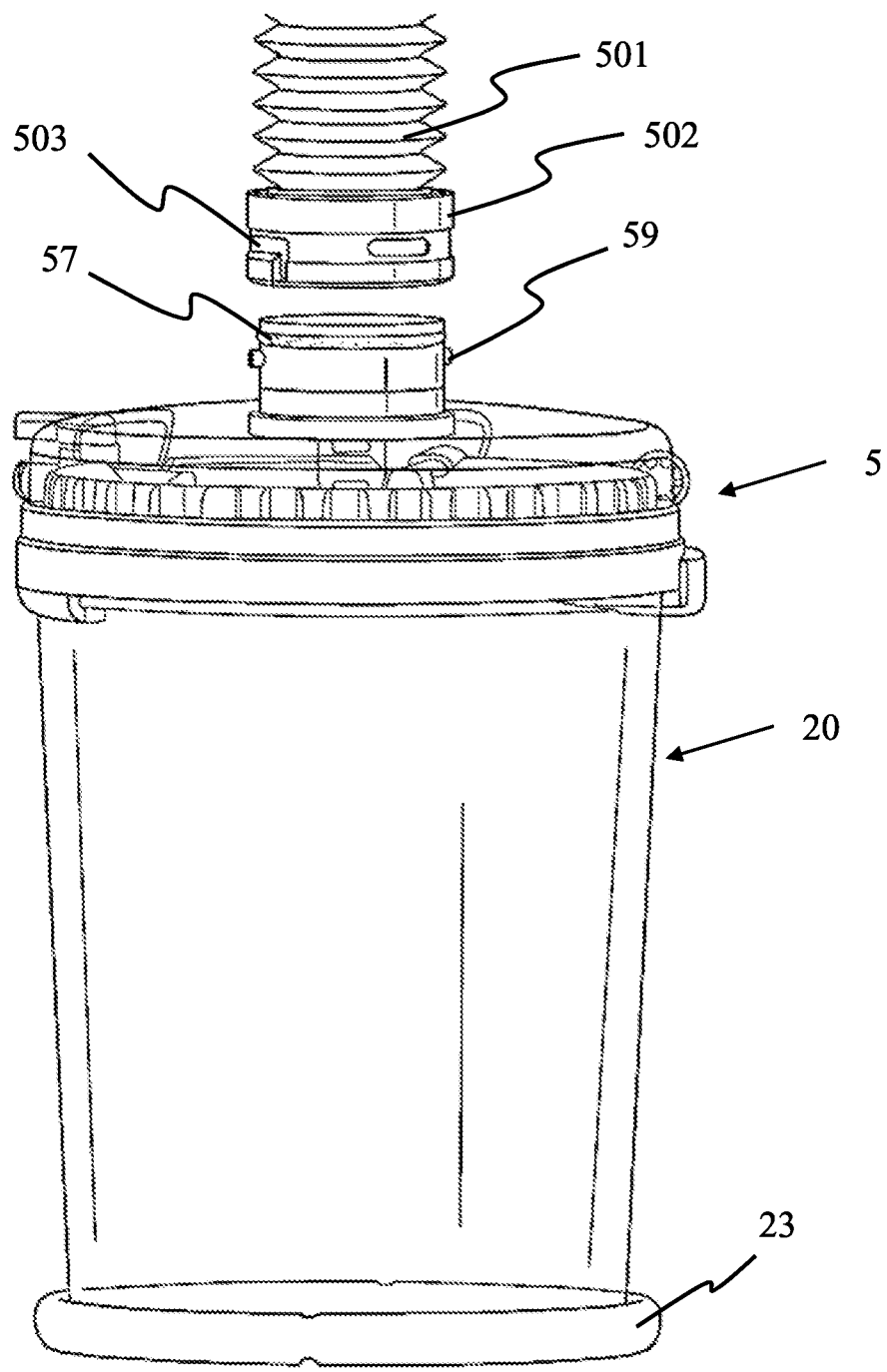
FIG. 23 is a perspective view of a surgical robotic access system in accordance with various embodiments with a robotic sleeve and with portions of the sealing cap shown transparent.

The outer access connector 58 in various embodiments provides a target area that is identifiable by the surgical robotic system to sense and/or locate for the insertion of a surgical robotic manipulator there through. In various embodiments, the outer access connector includes a robotic coupling interface configured to, engage, mate or sealingly mate with a corresponding robotic coupling interface of a robotic sleeve 500. In FIGS. 21-23, for example, the robotic coupling interface of the outer access connector includes a plurality of pins 59 and the robotic coupling interface of the robotic sleeve includes one or more slots 503 within a rotatable collar 502 to engage with the plurality of pins to form a bayonet like connection between the outer access connector and the robotic sleeve. In various embodiments, the robotic sleeve, the outer access connector or both includes a seal to seal the connection between the robotic sleeve and the robotic insertion tube. In one embodiment, the seal includes one or more compressible seals such as O-ring 57 disposed partially within one or more grooves in the outer surface of the outer access connector 58. In various embodiments, the robotic sleeve 500 is attached by a user to the outer access connector 58. The robotic manipulator, e.g., exemplary robotic instrument 504, is robotically controlled by a surgical robotic system autonomously or through assistance of a surgeon without a surgeon in direct contact or physically grasping the surgical robotic manipulator. In various embodiments, both the robotic sleeve and the robotic manipulators are robotically controlled. With the robotic sleeve 500 attached to the outer access connector 58, the surgical robotic system can identify or has a fixed or well-defined location of the surgical robotic access system and thus the opening in the patient. Additionally, the location is simplified by limiting the frame of reference relative to the patient. The surgical robotic manipulator can be maneuvered through the flexible robotic housing or tube 501 and collar 502 of the robotic sleeve 500 and into and through the surgical robotic access system without potential missteps as to the location of the opening of the patient.

In various embodiments, the outer access connector and inner access connector are integrated or locked together to form a single monolithic structure and/or made from the same material. In various embodiments, the outer access connector is adhered to the inner access connector. In various embodiments the outer access connector is removably coupled to the inner access connector, e.g., via snaps, tabs, pins, slots or other similar connections and as such the outer access connector can be removed if not needed or interchanged with another outer access connector with a different coupling interface as may be needed with a different robotic sleeve, manipulator or system. The robotic sleeve provides flexibility and/or protection to the surgical robotic manipulator extendable through and out the distal end of the sleeve. The outer access connector to the robotic sleeve connection ensures that the surgical robotic system remains connected to the surgical robotic access system and thus reduces or eliminates the need for the surgical robotic system to locate the opening in the patient or the surgical robotic access system.

The distal ends of the surgical robotic manipulator in various embodiments are removable and hot swappable with other distal ends of the surgical robotic manipulator that are arranged to preform specific surgical functions, such as stapling, electro-cautery, grasping, viewing, cutting and the like. In various embodiments, the outer access connector provides a fixed platform and seal for the robotic sleeve. The robotic sleeve remains static and in various embodiments the robotic coupling interface with the robotic sleeve and outer access connector also remains static. The surgical robotic manipulators can vary in shape and sizes and thus the inner access connector including the reduced or isolated flexible seal provides an adaptable yet static sealing arrangement to seal against the varied shapes and sizes of the surgical robotic manipulators or in the absence of a surgical robotic manipulator. The flexible seal also does not damage or disrupt the surgical robotic manipulator. The flexible seal surrounding the inner access connector also facilitates the seal with the opening in the body and allows freedom of movement of the outer access connector which facilitates the seal with or to robotic sleeve and manipulator and reduces potential damage to the robotic sleeve and/or manipulator due to off axis movements.

In various embodiments, a surgical robotic access system provides a double seal arrangement for a surgical robotic manipulator to be inserted there through or in the absence of a manipulator. The surgical robotic access system in various embodiments includes an outer access connector to removably attach to and seal with a robotic sleeve and an inner access connector to fixedly attach the outer and inner access connectors to a sealing cap attached to the patient and disposed over and sealing the opening in the patient. The flexible seal of the sealing cap in which the inner access connector is embedded or fixed allows freedom of movement of the outer and inner access connectors without adding stress or tension on the surgical robotic manipulator, robotic sleeve or the patient. The flexible seal within and/or below the inner access connector provides a seal for a surgical robotic manipulator to be inserted there through or in the absence of a manipulator inserted through the flexible seal. The reduced portion of the flexible seal defined and/or confined by the inner access connector provides a consistent density or consistency to provide a predefined or pre-known or predictable insertion force that may be used to generate haptic feedback or other similar sensor information to be recognized by the surgical robotics system to identify and/or simulate the insertion and withdrawal of the surgical robotic manipulator.

The sealing cap 5 of a surgical robotic access platform in various embodiments is incorporated with or removably attached to a retractor or protector 20 that provides retraction and/or protection of the incision or opening in the patient. In various embodiments, the retractor includes a sleeve, sheath or tube 22 extending between an inner ring 23 placed inside the patient and an outer ring 21 placed outside the patient. Both rings can be rigid, flexible or any combination thereof. The sheath is flexible and cylindrical. In various embodiments, the sheath has another shape, such as an oval or a more complex shape, is adjustable, is transparent or any combinations thereof. In various embodiments, the length of the sheath is adjustable by varying the location of the outer and inner rings or by gathering or winding portions of the sheath around the outer ring, the inner ring, an adaptor, other ring or the like and any combination thereof. In various embodiments, the sheath is non-adjustable defining a fixed length and diameter access channel. In various embodiments, the sheath includes one or more coatings such as a lubricious coating, anti-microbial coating or both. Examples of sealing caps, retractors and/or protectors are described in U.S. Patent Publication No. 2007/0088204 A1, the disclosure of which of incorporated by reference as if set forth in full herein. Examples of a flexible seal or material including gel material are described in U.S. patent application Ser. No. 10/381,220, filed Mar. 20, 2003, the disclosure of which is hereby incorporated by reference as if set forth in full herein.

In various embodiments, the sealing cap covers the proximal or outer portion of the retractor/protector. In various embodiments, the sealing cap provides additional access areas or portions. In the illustrated embodiment, the sealing cap includes a flexible seal or cover made of a flexible material, e.g., gel material, surrounding the robotic or central insertion tube and through which instruments may be inserted directly there through for additional access into the patient. In various embodiments, 12 mm and 5 mm removable access ports 38, 39 are provided for auxiliary surgical instruments or surgical robotic manipulators and are inserted around the robotic insertion tube. In various embodiments, the removable access ports comprise of a cannula with an attached or integrated seal assembly with an instrument seal, zero seal or both. The cannula in various embodiments having one or more support structures on the outer surface of the cannula to removably secure the removable access port to the flexible seal. In various embodiments, auxiliary surgical instruments are insertable directly through the flexible seal in portions around or adjacent the robotic insertion tube. The flexible seal provides a seal around or sealingly engages an outer surface of the surgical instruments as the instrument is inserted, utilized or withdrawn from the flexible seal around the inner access connector and a seal in various embodiments in the absence of a surgical instrument inserted in the flexible seal around the inner access connector.

The retractor/protector of a surgical robotic access platform provides a stable platform to connect the sealing cap to the patient. The stable platform allows movement of the robotic insertion tube without or reducing any additional movement or forces caused by any movement of the robotic insertion tube in the flexible seal. As such, the flexible seal reduces or dissociates movement of the flexible seal caused by movement of the robotic insertion tube relative to the rest of the sealing cap and the patient and the sealing cap attached to the retractor/protector further dissociates movement of the sealing cap on the patient caused by movement of the flexible seal of the sealing cap. The retractor/protector also atraumatically retracts the opening in the patient to increase range of access or mobility of the robotic manipulators and positions the tissue, around and through the opening, away from potential contact or trauma from the surgical robotic manipulators.

In various embodiments, an instrument shield or retractor shield 25 is provided to prevent or reduce potential damage to the retractor or protector and/or direct off-axis instruments towards the center or opening in the patient. In various embodiments, the sealing cap may be connected directly to the patient via sutures or adhesive and may be provided with or without the retractor, shield or both. In various embodiments, the surgical robotic access system provides access into a patient's body cavity for a 22 mm diameter surgical robotic manipulator. The surgical robotic access system provides a seal (zero-seal) when the robotic manipulator is not inserted through the surgical robotic access system. The surgical robotic access system also provides a seal (instrument seal) when the robotic manipulator is inserted through the surgical robotic access system. The seal prevents the loss or escape of fluids or gases. The surgical robotic access system in various embodiments also provides access for introducing or removing of gas or fluids such as insufflation gas, smoke or the like. The surgical robotic access system provides protection from distal tips of the robotic manipulator from damaging the surgical robotic access system. The surgical robotic access system in various embodiments provides auxiliary ports, e.g., a 5 mm, 12 mm or other dimensioned ports or access for similarly sized surgical instruments.

Figure 24:
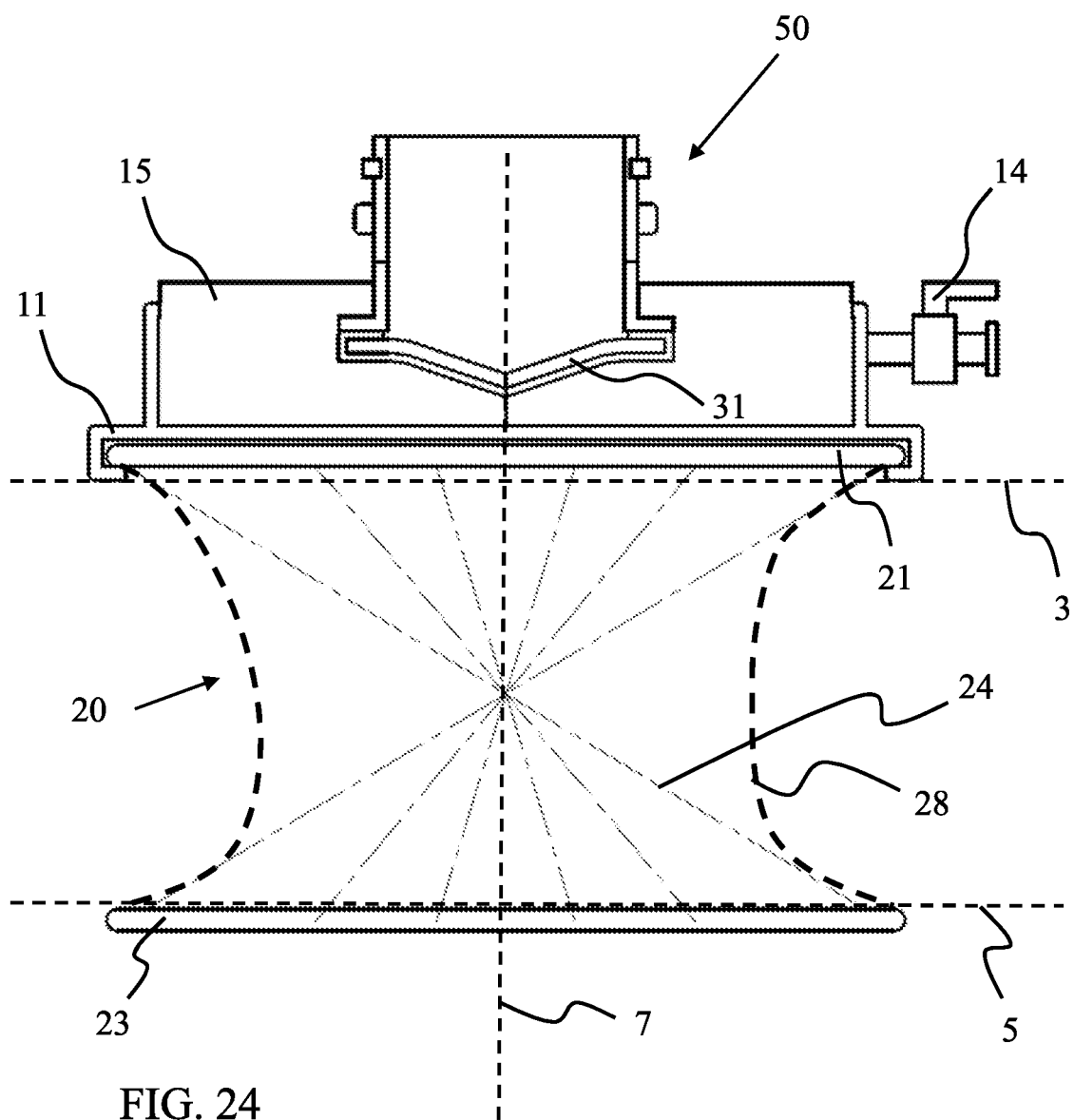
FIG. 24 is a cross-sectional view of a surgical robotic access system in accordance with various embodiments.
Figure 25:
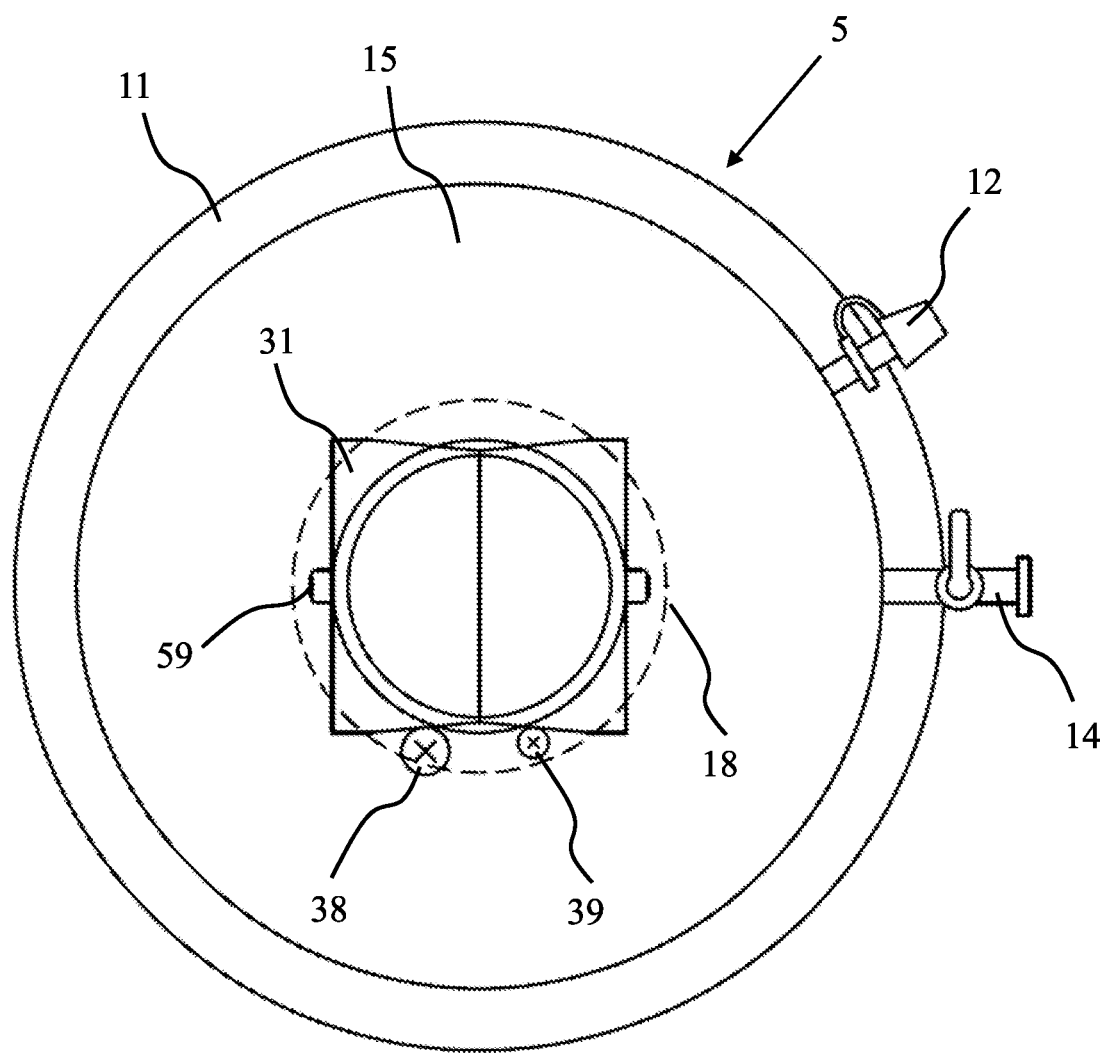
FIG. 25 is a top view of a surgical robotic access system in accordance with various embodiments.

In various embodiments, as shown for example in FIGS. 24-25, a surgical robotic access system is provided in which a sealing cap includes protectors or shield leaves 31 to protect the flexible seal 15 attached to or integrated with a ring, cap or cover 11. In various embodiments, the protectors are embedded in the flexible seal below the robotic insertion tube 50 and inside the inner periphery of the sealing cap 5. In various embodiments, the protectors are positioned between the distal end of the robotic insertion tube and the inner surface of the flexible seal. The protectors are confined within the area or space adjacent to the robotic insertion tube to allow additional access through the surrounding flexible seal as well as to allow freedom of movement of the flexible seal unencumbered or obstructed by the protectors. The flexible seal in one embodiment is a gel material and in various embodiments an upper surface of the protectors are exposed within the lumen of the robotic insertion tube and a lower and/or side surfaces of the protectors are surrounded by or directly attached and embedded in the flexible seal.

The protectors in one embodiment are cast into the flexible seal to protect or reinforce the flexible seal or material from being torn or punctured by the tips of the surgical robotic manipulators in such a way to effectively disrupt or make ineffective the zero sealing or instrument sealing capabilities of the sealing cap In various embodiments the protectors are made out of a soft and durable material, such as LDPE, to provide a lubricious surface for the tips of the robot manipulators to ride against during insertion or withdrawal of the robot manipulators. In various embodiments, the protectors are made from a material different, more durable and rigid or any combination thereof than the material of the flexible seal. In various embodiments, the protectors 31 are a plurality of planar curved or angled plastic or fabric sheets. In various embodiments, two protector sheets, each identical and mirror images of each other, meet together at an edge and in various embodiments over a midline of flexible seal or above the slit. The protectors having one edge elevated above the edge at the midline of the flexible seal provide a tapered entry to facilitate movement of the protectors and to direct the inserted robotic manipulator towards the slit in the flexible seal. In various embodiments, the flexible seal or material directly under the protectors are correspondingly shaped and sized to accommodate the shape and size of the protectors.

In various embodiments, the robotic insertion tube 50 comprises an outer access connector 58 that includes a robotic coupling interface such as bayonet pins and in various embodiments an inner access connector 55 connected to the outer access connector with the inner access connector cast or molded into the flexible material and in various embodiments above the protectors. The outer access connector in various embodiments has an O-ring fitted around the outer periphery of the outer access connector to provide a seal with a mating end or robotic coupling interface of a surgical robotic sleeve. The outer access connector as such maintains a seal with the robotic sleeve even when the seal in the flexible seal is disrupted by the insertion of a robot manipulator.

Figure 26:
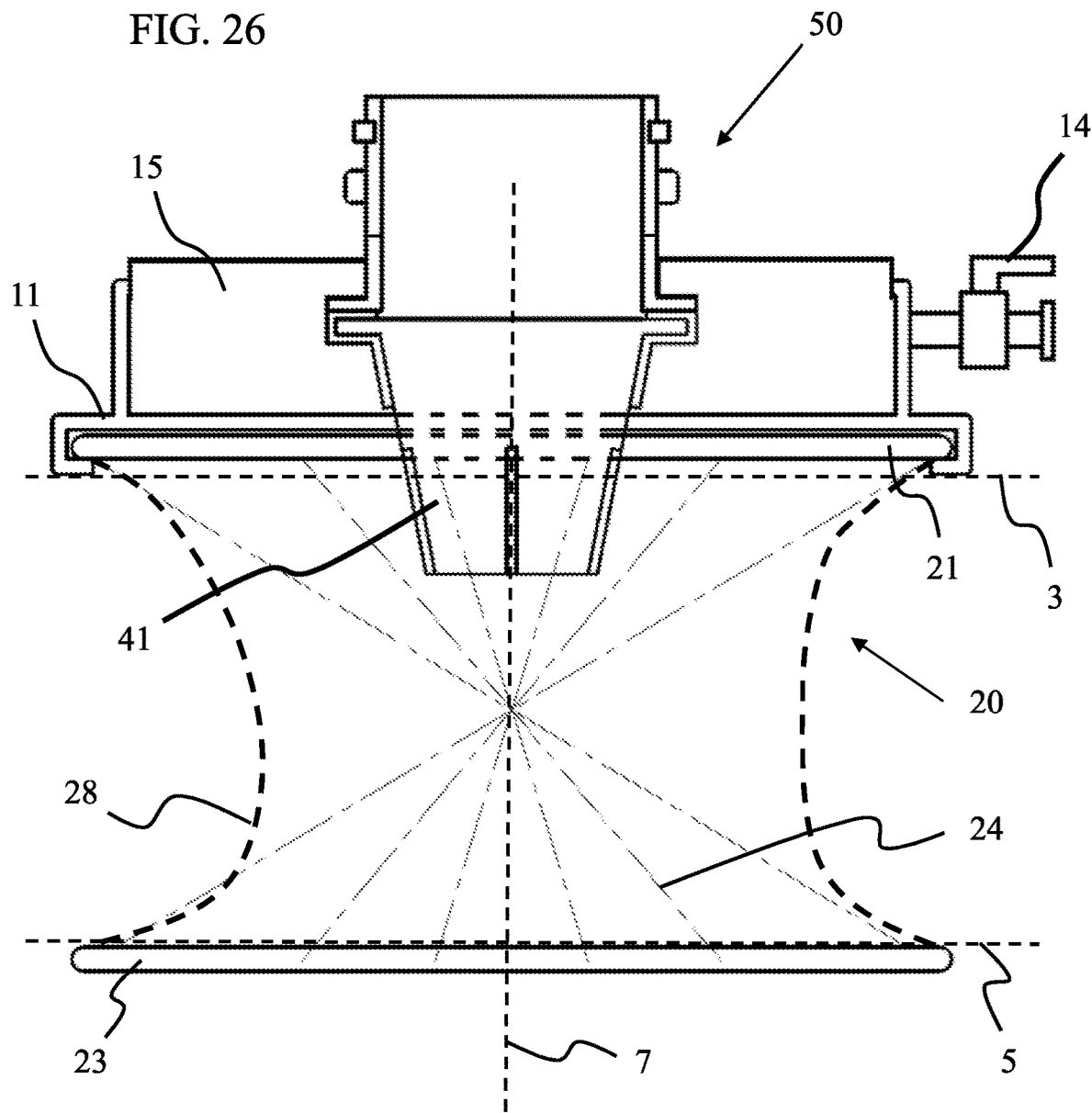
FIG. 26 is a cross-sectional view of a surgical robotic access system in accordance with various embodiments.
Figure 27:
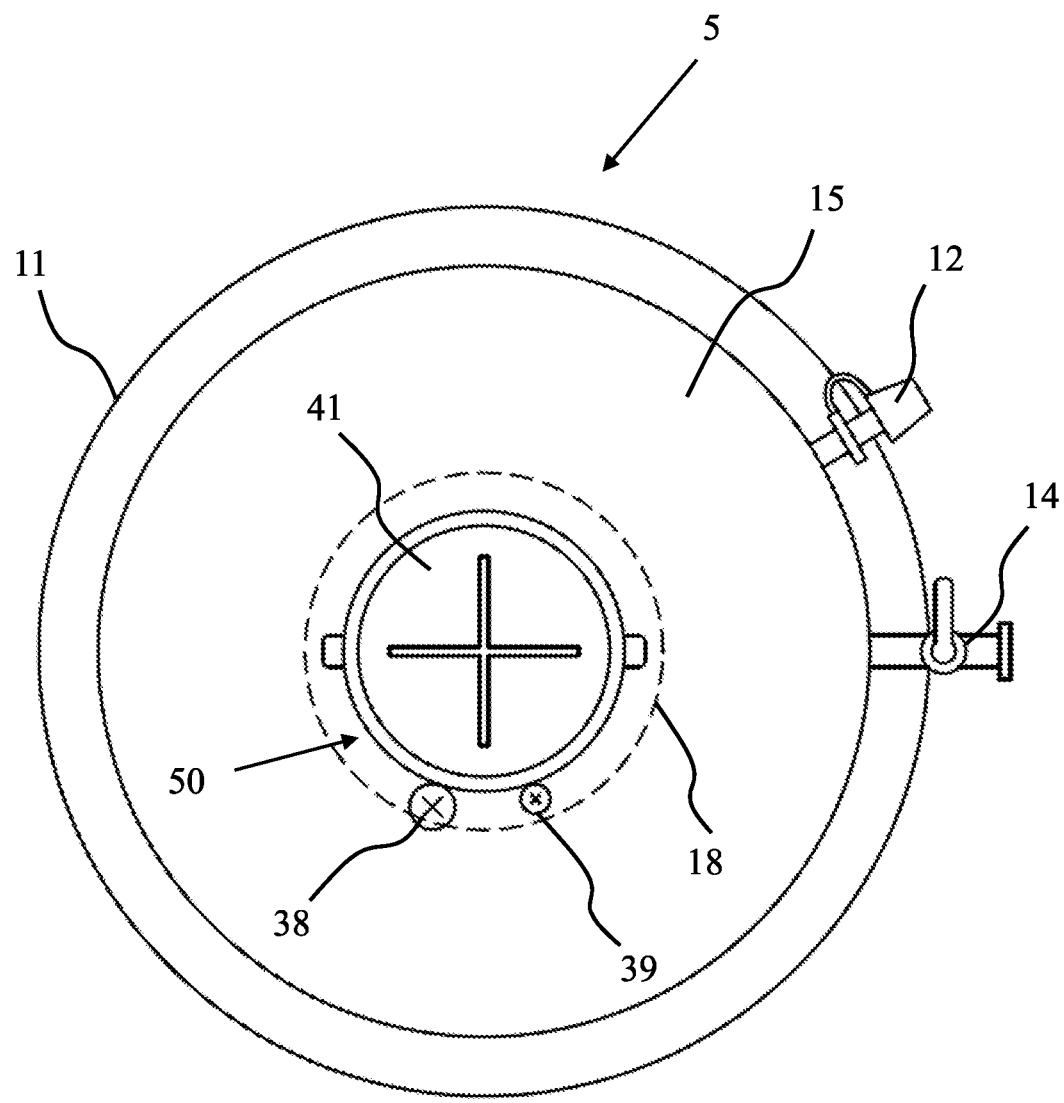
FIG. 27 is a top view of a surgical robotic access system in accordance with various embodiments.

In various embodiments, as shown for example in FIGS. 26-27, a double duckbill seal 41 is cast into the flexible seal 15 to provide an additional or separate zero seal or seal in absence of a surgical robotic manipulator. The duckbill seal in various embodiments is made of a material different from the material of the flexible seal 15. The duckbill seal is compressible by the surrounding flexible seal to further enhance the seal of the duckbill seal. In various embodiments, the duckbill seal does not extend through the flexible seal and instead is completely embedded in the flexible seal to further enhance the seal of the sealing cap and the duckbill seal. The protectors, illustrated in FIGS. 24-25, may be included and may proceed the duckbill seal.

Figure 28:
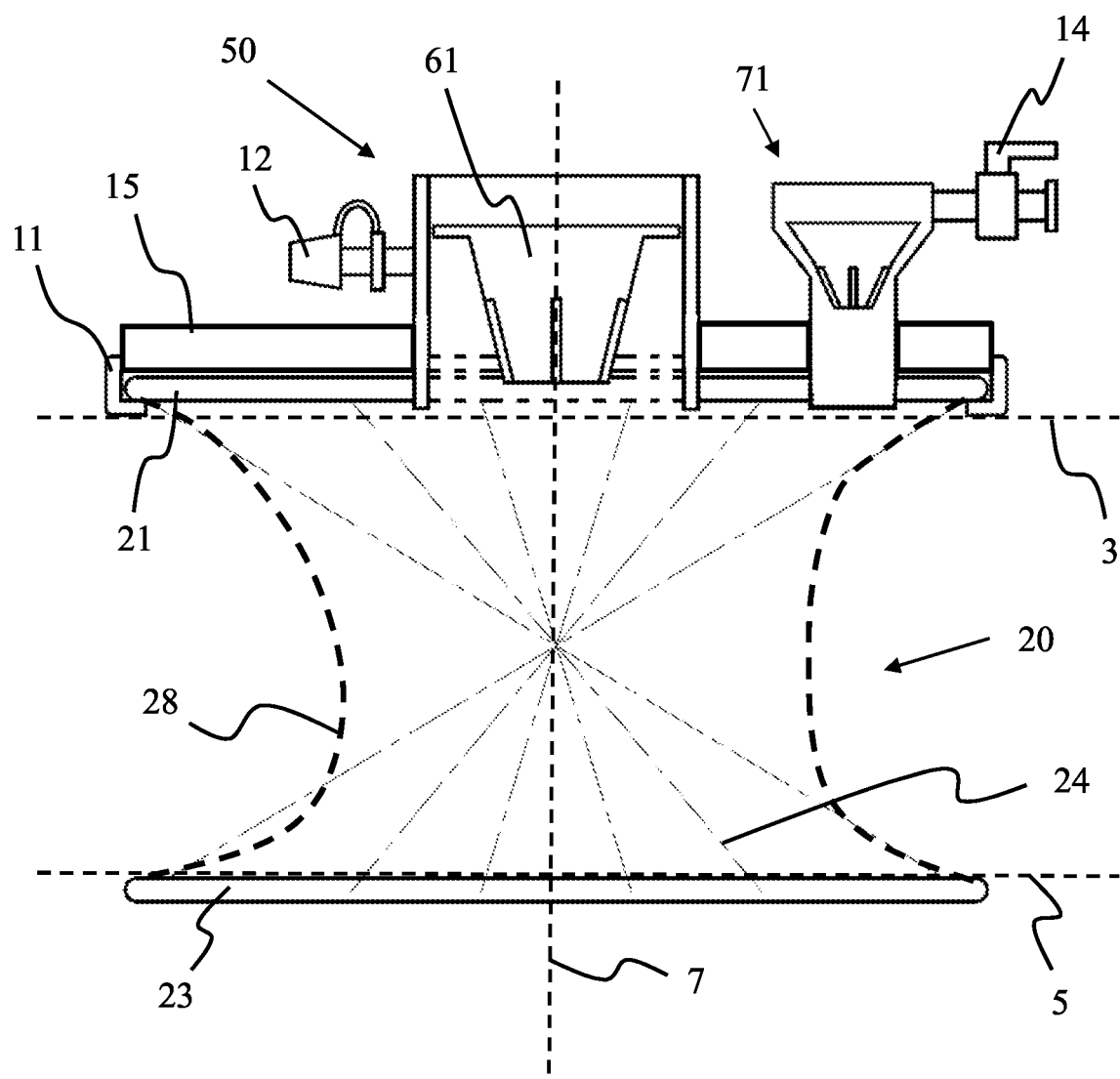
FIG. 28 is a cross-sectional view of a surgical robotic access system in accordance with various embodiments.
Figure 29:
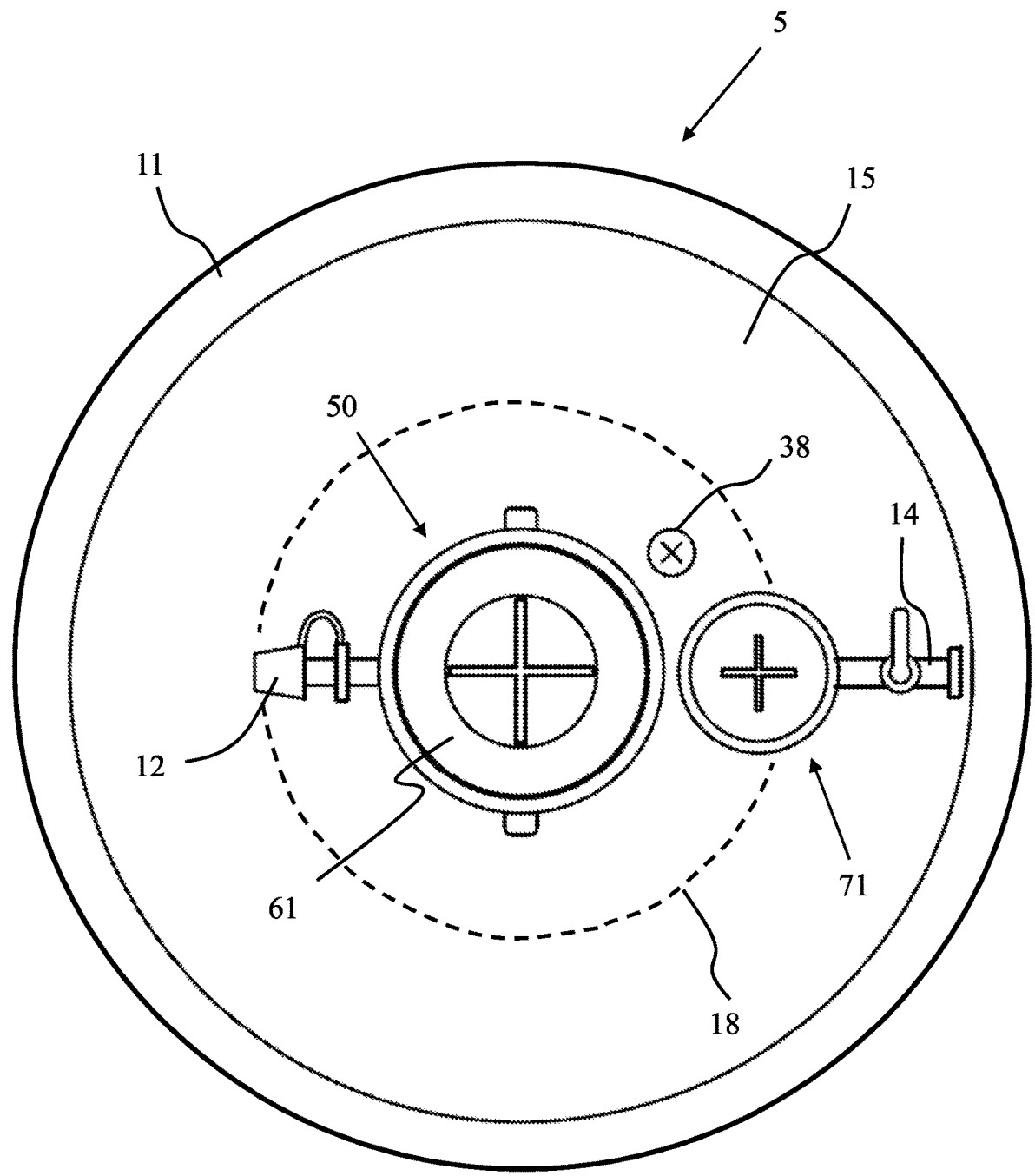
FIG. 29 is a top view of a surgical robotic access system in accordance with various embodiments.

In various embodiments, as shown for example in FIGS. 28-29, a surgical robotic access system is provided including robotic insertion tube 50 embedded in a flexible seal 15 of a sealing cap 5, 12 mm trocar or access port 71 with an additional stopcock 14 and a simplified/exemplified 5 mm auxiliary port 38. In various embodiments, the robotic insertion tube includes a duckbill seal 61 that provides a separate or additional zero seal for the robotic insertion tube. In the illustrated embodiment, the robotic insertion tube 50 includes an evacuation and/or insufflation port 12 to remove or introduce gas, e.g., insufflation gas, to or from an external source through the robotic insertion tube and from or into the patient's body cavity. As such, the duckbill seal also provides a zero seal as gas or fluids are removed and/or introduced. In various embodiments the robotic insertion tube and the access ports are utilized together to increase triangulation manipulation or viewing for the surgical procedure.

In accordance with various embodiments, the dashed line 18 represents an exemplary incision size of the patient and in which the robotic insertion tube and the other ports are delimited or confined within. The dashed lines 24 represents or exemplifies the protector and its film or sheath that may be twisted prior to its insertion into the opening in the patient. The film twisted can further assist in sealing the opening of the patient. In various embodiments, the dashed lines 28 represent or exemplify the body wall and the sheath of the retractor retracting the opening in the patient to ease access into the patient. In the illustrated embodiments, one or more of the components are shown transparent or translucent to better show some of the underlying components or features otherwise hidden by the flexible seal or sealing cap or other portions thereof. In various embodiments, the dashed line 18 outlines or exemplifies a different consistency or flexibility of the flexible seal relative to the surrounding material and in various embodiments the flexible seal within the dashed line 18 is firm or more rigid relative to the surrounding material and thus moves or translates freely relative to the ring while the robotic insertion tube remains static relative to the flexible seal immediately surrounding the tube. The dashed lines 3, 5 generally represent or exemplify the upper and lower surfaces of the body wall of a patient. The dashed line 7 represents or exemplifies the mid-line or longitudinal axis of the surgical robotic access system and in various embodiments represents an initial incision or opening in the patient.

In the illustrated embodiments, it is exemplified that the sealing cap may have different sizes and dimensions along with the robotic insertion tube. The dimensions and sizes may be dictated or determined based on the surgical procedures or the surgical robotic system. Similarly, the shape and materials of the access system may vary to optimize the surgical site space or connectivity to the surgical robotic system. The robotic or central insertion tube although provided as a tube or cylindrical may be of varied shapes and dimensions such as hour-glass, frustoconical or the like to optimize the surgical site space or sealing engagement with surgical robotic instruments or the sealing cap.

In various embodiments, the surgical robotic access system provides a consistent outer access connector and seal for a robotic sleeve and a consistent inner access connector and seal for a surgical robotic manipulator. Throughout a surgical procedure, the surgical robotic manipulator may be interchanged with other surgical robotic manipulator each having differing or varying geometry and/or dimensions.

The above description is provided to enable any person skilled in the art to make and use the surgical robotic access system described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth. It is therefore also to be understood that the system or devices may be practiced otherwise than specifically described, including various changes in the size, shape and materials. Thus, embodiments described should be considered in all respects as illustrative and not restrictive.

The invention claimed is:

1. A surgical robotic access system providing robotic manipulator access into a patient's body, the surgical robotic access system comprising:
   a sealing cap disposed externally to a patient's body, the sealing cap including a ring, a flexible seal and at least one shield leaf, the flexible seal attached to the ring and the at least one shield leaf embedded in the flexible seal, the flexible seal and the at least one shield leaf disposed within an inner periphery of the ring;
a retractor comprising an outer ring removably connected to the ring of the sealing cap and an inner ring arranged to be positioned within a patient's body;
a robotic sleeve; and
a robotic insertion tube comprising a proximal end and a distal end, the proximal end removably connected to the robotic sleeve and the distal end embedded and permanently affixed in the flexible seal of the sealing cap, the robotic insertion tube having a lumen extending from a proximal opening at the proximal end of the robotic insertion tube to a distal opening at the distal end of the robotic insertion tube, the flexible seal disposed around and under the distal end of the robotic insertion tube encompassing the distal end of the robotic insertion tube and covering the distal opening at the distal end of the robotic insertion tube, through which a surgical robotic manipulator insertable through the lumen is insertable through the at least one shield leaf and the flexible seal covering the distal opening at the distal end of the robotic insertion tube.

2. The system of claim 1 wherein the at least one shield leaf comprises an upper surface exposed within the lumen of the robotic insertion tube and a lower surface surrounded by and embedded in the flexible seal.

3. The system of claim 1 wherein the at least one shield leaf is disposed directly under the distal opening at the distal end of the robotic insertion tube.

4. The system of claim 3 wherein the flexible seal is made of gel material.

5. The system of claim 4 wherein the at least one shield leaf has a lubricious surface.

6. The system of claim 4 wherein the at least one shield leaf is more rigid than the flexible seal.

7. The system of claim 4 wherein the at least one shield leaf is made of a material different from the flexible seal.

8. The system of claim 7 wherein the at least one shield leaf is a planar angled fabric sheet.

9. The system of claim 7 wherein the at least one shield leaf is a planar angled plastic sheet.

10. The system of claim 9 wherein the at least one shield leaf comprises a first shield leaf and a second shield leaf, both the first and second shield leaves being identical and mirror images of each other.

11. The system of claim 10 wherein the first and second shield leaves meet together at an edge and over a midline of the flexible seal.

12. The system of claim 10 wherein the first and second shield leaves meet together at an edge and over a slit in the flexible seal.

13. The system of claim 12 wherein the proximal end of the robotic insertion tube includes a plurality of pins extending form an outer surface and periphery of the proximal end of the robotic insertion tube.

14. The system of claim 13 wherein the robotic sleeve has at least one slot to engage at least one pin of the plurality of pins of the robotic insertion tube and removably couple and sealingly engage the proximal end of the robotic insertion tube to the robotic sleeve.

15. The system of claim 14 wherein the proximal end of the robotic insertion tube includes an o-ring disposed around the outer surface and periphery of the proximal end of the robotic insertion tube.

16. The system of claim 12 further comprising a plurality of removable access ports insertable through the flexible seal and disposed around the robotic insertion tube, the plurality of removable access ports including a first removable access port and a second removable access port, the first removable access port being larger than the second removable access port.

17. The system of claim 16 wherein the first removable access port comprises a cannula, an instrument seal and a zero seal.

18. The system of claim 17 further comprising an insufflation port disposed through the ring and the flexible seal.

19. The system of claim 18 wherein portions of the flexible seal near and directly surrounding the robotic insertion tube is raised relative to portions of the flexible seal near the ring of the sealing cap, the portions of the flexible seal near and directly surrounding the robotic insertion tube having a thickness greater than a thickness of the portions of the flexible seal near the ring of the sealing cap.

20. The system of claim 19 wherein a distal most end of the robotic insertion tube is disposed above a lower surface of the flexible seal.

* * * * *